United States Patent [19]

Bæk et al.

[11] Patent Number: 5,591,628
[45] Date of Patent: Jan. 7, 1997

[54] METHOD OF DETERMINING THE PRESENCE OF ENDOTOXIN IN A SAMPLE

[76] Inventors: Leif Bæk, Heinesgade 1, 4.tv., 2200 Copenhagen N; Claus Koch, Overgaden oven Van-det 26.1, 1415 Copenhagen K, both of Denmark

[21] Appl. No.: 68,178

[22] Filed: May 28, 1990

Related U.S. Application Data

[62] Division of Ser. No. 295,213, filed as PCT/DK88/00081, May 19, 1988, Pat. No. 5,316,911.

[30] Foreign Application Priority Data

May 20, 1987 [DK] Denmark ................................ 2558/87

[51] Int. Cl.$^6$ ................................................. C12N 5/16
[52] U.S. Cl. .................. 435/240.26; 435/7.1; 435/7.8; 435/7.92; 435/240.27; 436/548; 530/388.1; 530/389.1
[58] Field of Search ..................... 436/548; 530/387.1, 530/388.26, 388.1, 389.1; 435/7.21, 7.9, 7.4, 7.32, 7.5, 8, 12, 23, 27, 28, 188, 7.1, 7.92, 7.8, 240.1, 240.26, 240.27

[56] References Cited

U.S. PATENT DOCUMENTS

| | | |
|---|---|---|
| 4,281,061 | 7/1981 | Zuk et al. . |
| 4,414,336 | 11/1983 | Watanabe et al. . |
| 4,495,294 | 1/1985 | Nakahara et al. . |
| 4,520,111 | 5/1985 | Miller ........................................ 435/18 |

OTHER PUBLICATIONS

Levin et al, "Clottable Protein in Limulus: Its Localization and Kinetics of Its Coagulation by Endotoxin", pp. 186–197 (1986).
Levin et al, Bull. Johns. Hopkins Hosp., 115, pp. 337–345 (1964).
Bang, Bull. Johns. Hopkins Hosp., 98, pp. 325–351 (1958).
Jorgensen et al, Proc. Soc. Exp. Biol. Med., 146, pp. 1204–1031 (1974).
Fleishman et al, Prog. Clin. Biol. Res., 93, pp. 131–140 (1982).
Weary et al, Appl. Environ. Microbiol., 40, pp. 1148–1151 (1980).
Solum, Thromb. Res., 2, pp. 55–70 (1973).
Liu et al, Biomedical Applications of the Horseshoe Crab (Limulidae)(ed. E. Cohen), N.Y.: Alan R. Liss, pp. 147–158 (1979).
Holme et al, J. Ultrastructure Res., 44, pp. 329–338 (1973).
Tai et al, J. Biol. Chem., 252, pp. 4773–4776 (1977).
Nakamura et al, B. Biochem. and Biophys. Res. Commun., 72, pp. 902–908 (1976).
Nakamura et al, J. Biochem., 80, pp. 649–652 (1976).
Gaffin, Biorheologi, 13, pp. 273–280 (1976).
Shishikura et al, J. Exp. Zool., 223, pp. 89–91 (1982).
Tai et al, J. Biol. Chem., 252, pp. 2178–2181 (1977).
Nakamura et al, Biochim. Biophys. Acta., 707, pp. 217–225 (1982).
Nakamura et al, Biochem. Biophys. Res. Commun., 108, pp. 1619–1623 (1982).
Liang et al, J. Biol. Chem., 255, pp. 5586–5590 (1980).
Tanaka et al, Biochem. Biophys. Res. Comm., 105, pp. 717–723 (1982).
Kakinuma et al, Biochem. Biophys. Res. Commun., 101, pp. 434–439 (1981).
Morita et al, FEBS Letters, 129, pp. 318–321 (1981).
Albaugh et al, Endotoxins and their detection with the Lumulus lysate test. N.Y.: Alan R. Liss, pp. 183–194 (1982).
Fujita et al, Endotoxins and their detection with the Limulus lysate test., N.Y.: Alan R. Liss, pp. 173–182 (1982).
Nandan et al, J. Lab. Clin. Med., 89, pp. 910–918 (1977).
Dubczak, et al, Biomedical Applications of the Horseshoe Crab (Limulidae), N.Y.; Alan R. Liss, pp. 403–414 (1979).
Jorgensen et al, J. Parenter. Sci. Technol., 36, pp. 96–94 (1982).
Ditter et al, Prog. Clin. Biol. Res., 93, pp. 385–392 (1982).
Frauch, J. Pharm. Sci., 63, pp. 808–809 (1974).
Goto et al, Jpn. J. Exp. Med., 47, pp. 523–524 (1977).
Goto et al, Jpn. J. Exp. Med., 49, pp. 19–25 (1979).
Melvaer et al, Appl. Environ. Microbiol., 43, pp. 493–494 (1982).
Flowers, Med. Lab. Sci., 36, pp. 171–176 (1979).
Okuguchi, Microbiol. Immunol., 22, pp. 113–121 (1978).
Kreeftenberg et al, Dev. Biol. Standard, 34, pp. 15–20 (1977).
Gardi et al, Anal. Biochem., 109, pp. 382–385 (1980).
Harris et al, Biomedical Applications of the Horseshoe crab (Limulidae), N.Y.: Alan R. Liss, pp. 265–274 (1979).
Munford, Anal. Biochem., 91, pp. 509–515 (1978).
Baek et al, J. Clin. Microbiol., 17, pp. 1013–1020 (1983).
Elin et al, J. Infect. Dis., 128, pp. 349–352 (1973).
Wildfeuer et al, Appl. Microbiol., 28 pp. 867–871 (1974).
Brunson et al, Infect. Immun., 14, pp. 1256–1258 (1976).
Mikami et al, Microbiol. Immunol., 26, pp. 403–409 (1982).
Platica et al. Experientia, 34, pp. 1154–1155 (1978).
Fine et al. J. Dent. Res., 56, p. 1500 (1977).
Weinberg et al, Biochem. Biophys. Res. Commun., 97, pp. 493–499 (1980).
Smith et al, Ann. Allergy, 40, pp. 12–14 (1978).
Lewis et al, J. Gen. Microbiol., 114, pp. 215–216 (1979).
Felton et al, J. Parasitol., 66, pp. 846–847 (1980).
Wexler et al, Infect. Immun., 23, pp. 845–857 (1979).
Elin Biomedical Applications of the Horseshoe Crab (Limulidae), N.Y.: Alan R. Liss, pp. 279–292 (1979).
Tubbs, Trans. R. Soc. Trop. Med. Hyg., 74, pp. 121–123 (1980).
Galloway et al, Am. J. Med., 63, pp. 933–938 (1977).
Obayashi et al, Clinica Chimica Acta, 149, pp. 55–65 (1985).
Nakamura et al, Eur. J. Biochem., 154, pp. 511–521 (1986).

(List continued on next page.)

*Primary Examiner*—Christine M. Nucker
*Assistant Examiner*—Jeffrey Stucker
*Attorney, Agent, or Firm*—Birch, Stewart, Kolasch & Birch, LLP

[57] ABSTRACT

There is disclosed a method for determining the presence of endotoxin or an endotoxin like substance in a sample, as well as a monoclonal antibody and test kit useful in the method.

27 Claims, 10 Drawing Sheets

OTHER PUBLICATIONS

Nakamura, T. et al. Purification and properties of intracellular clotting factor, Factor B., from horshoe Crab (*Tachypleus tridentatus*) Hemocytes. J. Biochemistry 99 (3):847–857, 1986(a).

Maurer, P. H. et al. Proteins and polypeptides as antigens. Methods in Enzymology 70: 49–70, 1980.

Roche, A–C., et al. Limulin (*Limulus Polyphemus*)Lectin): Mitogenic effect on human peripheral lymphocytes. Eur. J. Immunol 7:263–267, 1977.

Tijssen, P. Practice and Theory of Enzyme Immunoassays. New York: Elsevier. Ch. 10 (pp. 173–219) and Ch. 13 (pp. 296–328), 1985.

Van Dyke, K., ed. Bioluminescence and Chemiluminescence: Instruments and Applications, vol. II. Boca Raton, FL: CRC Press. pp. 168–169, 1985.

Zhang, G. et al. New Microassay for quantification of endotoxin using *Limulus* amebocyte lysate combined with an enzyme–linked immunosorbent assay. J. Clin. Microbiol. 26(8): 1464–70, 1988.

Brandin, E. R. et al. Polyphemin: A techoic–acid binding lectin from the horseshoe crab, *Limulus polyphemus*. Biochemical and Biophysical Research Communications 113(2): 611–617, 1983.

Rose, N. R. et al., eds. Manual of Clinical Laboratory Immunology, 3rd Edition Washington, D.C.: American Society for Microbiology. Ch. 16 (Dauphinais, R. M., ed.); Chapter 17 (Voller, A., et al., eds.); Chapter 18 (Larsen, J. et al., eds.); pp. 88–115, 1986.

Joklik et al, eds. Medical Microbiology. Norwalk, Connecticut: Appleton–Century Crofts, 1984, pp. 103–105.

Draft Guideline For Validation of the Limulus Amebocyte Lysate Test as an End Product Endotoxin Test for Human and Animal Parenteral Drugs, Biological Products and Medical Devices; FDA, Feb. 2, 1983, Pharmacopedial Forum. 9, 3012–3021.

M. Ohki et al., FEBS. Letters, vol. 120, No. 2, Nov. 1980, pp. 217–220.

Prior et al., Journal of Clinical Microbiology, vol. 10, No. 3, Sep. 1979, pp. 394–395.

M. Suzuki et al., Microbiol. Immunol., vol. 21(8), 419–425, 1977.

R. C. Seid, Jr. et al., Infection and Immunity, Sep. 1980, vol. 29, No. 3, pp. 990–994.

J. H. Jorgensen, Handbook of Endotoxin, vol. 4, 1986, pp. 127–160, Elsevier Science Publisher, B. V., Amsterdam.

M. B. Wilson, et al., "Immunofluorescence and Related Staining Techniques" (W. Knapp et al., eds.), pp. 215–224. Elsevier/North–Holland, Amsterdam (1978).

METHOD OF DETERMINING THE PRESENCE OF ENDOTOXIN IN A SAMPLE

This application is a divisional of application Ser. No. 07/295,213, filed on Jan. 6, 1989, now U.S. Pat. No. 5,316,911, the entire contents of which are hereby incorporated by referencing.

FIELD OF THE INVENTION

The present invention relates to a method of determining the presence of endotoxin or endotoxin-like substances in a sample, as well as to a monoclonal antibody and test kit useful in the method.

BACKGROUND OF THE INVENTION

The horseshoe crabs *Limulus polyphemus, Tachypleus tridentatus, Tachypleus gigas* and *Carcinoscorpius rotundicauda* are phylogenetically primitive marine arthropods which have not evolved significantly over the past 300 million years (1).

The horseshoe crab has an open circulatory system containing blue haemolymph, and the only formed element present in the haemolymph is a cell called the amoebocyte (2).

The use of the Limulus amoebocyte lysate (LAL) as an in vitro test for endotoxin resulted directly from the important observation made by Bang (3). He observed that the horseshoe crab underwent a type of disseminated intravascular coagulation (DIC) when generalized infection occurred with marine gram-negative bacteria. This initial in vivo observation was later extended by the discovery that clotting of Limulus hemolymph could be produced in vitro by addition of either viable gram-negative bacteria or purified endotoxin from the cell wall of gram-negative bacteria (2). It was also discovered by the same researchers (1) that the amoebocyte was the source of all of the factors necessary for hemolymph coagulation.

The current application of the test as an in vitro assay for endotoxin is based on the fact that physical disruption of amoebocytes which have been isolated from the haemolymph by centrifugation yields a suspension (LAL) containing the coagulation components which may then only be activated by bacterial endotoxin. Application of this principle has made the LAL test the most sensitive method available for the detection of gram-negative bacteria, endotoxin and lipopolysaccharide (LPS). LAL prepared by current purification methods can reliably detect 0.1 ng/ml of purified *Escherichia coli* standard endotoxin. LAL has been shown to detect either bound (cell-associated) or free endotoxin (4) incorporated in the cell walls of virtually all gram-negative bacteria. However, endotoxin prepared by different extraction procedures, from different species, may vary widely in reactivity (5,6). For these reasons, a reference standard endotoxin (RSE) has been prepared by the U.S. Food and Drug Administration (USFDA) as a means for standardization of LAL and rabbit pyrogenicity tests (Unites States Pharmacopoeia XX) (7).

Amoebocyte lysate of similar reactivity to endotoxin can be prepared from all 4 species of horseshoe crabs.

The clotting processes in Limulidae

The currently known clotting processes in Limulidae are summarized in Table 1.

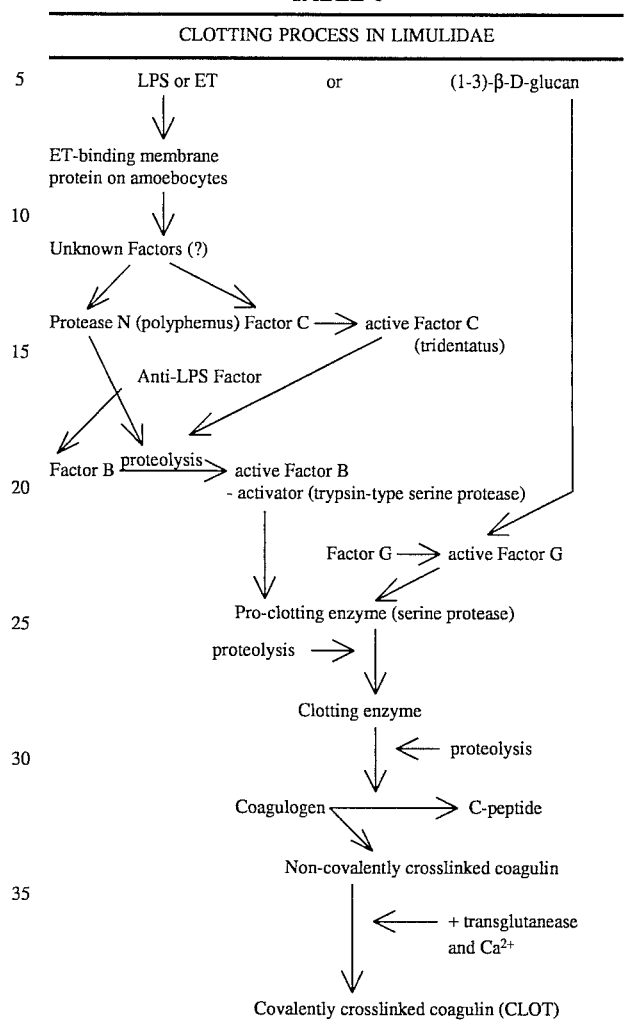

TABLE 1
CLOTTING PROCESS IN LIMULIDAE

Cellular coagulogen: Coagulogen consists of a polypeptide chain with internal disulfide bonds which are important for the stability of the polymerizable form of the molecule (8). In *Limulus polyphemus*, coagulogen was found to consist of 220 amino acids with half-cystine content of 18 residues (9). No free SH group was detected; glycine appears to be the only N-terminal residue, and serine its C-terminal residue (9). Coagulogen is always converted by a serine protease enzyme. After clotting, the gel protein displays a helical structure in electron microscopy (10). In *Tachypleus tridentatus*, the coagulogen comprises 132–135 amino acids including high levels of basic amino acids, with N-terminal alanine and C-terminal phenylalaine. In Limulus, clot formation seems to involve the cleavage of the single Arg-Lys peptide bond on the coagulogen (11,9). The N-peptides interact among themselves in a non-covalent fashion to form the insoluble clot. In *Tachypleus tridentatus*, the enzymatic formation of gel involves limited proteolysis of the Arg-Gly and Arg-Thr peptide linkages located in the N-terminal portion of coagulogen, thus releasing peptide (12,13). The C-fragment of Limulus mainly contains glutamic and aspartic acids (14). Whereas Liu et al. (9) detected a C-peptide with 45 amino acids in this species, Nakamura et al. (13) and Shishikura et al. (15) claimed that this C-peptide had 28 amino acid residues arranged in a species-specific sequence.

Clotting enzyme: The clotting enzyme is a serine protease enzyme. It exists in two active forms with molecular weights of 78,000 and 40,000, respectively, and a very similar amino acid composition, indicating a monomer-dimer relationship (9). In *Tachypleus tridentatus*, the unreduced clotting enzyme is described as a glycoprotein with a molecular weight of 42,000 which aggregates to form a protein with a MW of 350,000. The clotting enzyme originates from an inactive pro-clotting enzyme. Pro-clotting enzyme can be active via two independent pathways (Table 1): by the LPS of gram-negative bacteria, or by the (1–3)-β-D-glucans from the cell walls of certain fungi and algae.

LPS-mediated coagulation: Firstly, it was demonstrated that endotoxin or LPS activates a pro-clotting enzyme of the serine protease type (16,11). Secondly, an additional Factor B or pro-activator was also found to be involved in the LPS-induced coagulation of LAL since it activated the pro-clotting enzyme (17,18). This activation probably involves limited proteolysis, i.e. of an arginyl or lysyl-X bond of the pro-clotting enzyme (18). Finally, this pro-activator was observed to be converted to an active Factor B or activator (i.e. trypsin-type serine protease) by another proteolytic enzyme called protease N (Factor C in *T. tridentatus*) which seems to be LPS-dependent (18,19). These successive findings indicate that this coagulation process represent a complex enzyme cascade which might also include other unknown factors (Table 1).

Anti-clotting factors: An 80 Kd protein form the amoebocyte membrane specifically binds the endotozin or LPS (9,20). According to the authors, this receptor protein can recognize and immobilize small quantities of LPS in Limulus blood without massive intravascular coagulation. In addition, an anticoagulant (anti-LPS factor) which inhibits LPS-inducted coagulation is present in the amoebocytes from the hemolymph of *Tachypleus tridentatus* and *Limulus polyphemus* (21). This anticoagulant inhibits the activation of Factor B, but not its activity. The other mediated coagulation pathway is not affected by the anti-LPS factor (21).

(1–3)β-D-glucan-mediated coagulation: Both the antitumor agent -(1–3)-β-D-glucan and other antitumor polysaccharies have a potent ability to cause gelatin of LAL (22) by activating a factor G which acts on pro-clotting enzyme (23).

Different Methods for Detecting Endotoxin by LAL

By far the most frequently used method is the clot test. This method is based on the fact that the end result of the cascade of reactions in LAL when reacting with endotoxin is an opaque gel or clot. The test is performed as follows: 0.1 ml of LAL is mixed with 0.1 ml of test solution in a test tube. The mixture is incubated at 37° C. in a water bath for one hour. The test is recognized as positive when a clot is formed and the clot is stable when the test tube is inverted 180°. Less intense reactions have been described, which manifest as an increase in viscosity, appearing as starch-like granules which adhere to the wall of a test tube, often accompanied by an increased opacity. The subjectivity of interpreting endpoints of less than complete gelation has been a point for criticism of this method of performing the test. This is especially true when clinical specimens are tested because of interference of various substances.

Based on the above-mentioned studies of the reaction mechanism in LAL, other modifications of the LAL test have been published. These include a turbidometric (24), a chromogenic (25), a colorimetric (26), a nephelometric (27), kinetic methods (28-14 30), different slide methods (31–36), capillary tube methods (38,39), microdilution (40), LAL-based (41), radioisotopic labelling of coagulogen (42) and an immunoelectrophoretic method which measures the loss of antigenicity of coagulogen when it is cleaved by the LPS-activated enzyme (43). In all these methods, except the immunolectrophoretic method (43), the test result is read visually or indirectly by means of some sort of equipment.

Specificity of LAL for Endotoxin

The specificity of the LAL reaction for endotoxin or LPS has been questioned by several investigators. It has been reported that thrombin, thromboplastin, and certain synthetic polynucleotides all resulted in a positive LAL test (44). Peptidoglycans from gram-positive bacterial (45), exotoxins derived from group A Streptococci (46), several simple polysaccharides, including yeast mannans and bacterial dextrans (47), synthetic dextran derivatives (48), and dithiols (49), cause gelation of LAL.

The LAL test has been used to determine the biological activity of endotoxin-like molecules purified from the membrane material of various organisms. Positive LAL tests were obtained with lipoteichoic acid from *Streptococcus faecalis* (50), lipoglycans from different strains of Mycoplasma (51,52), cell wall fractions from *Micropolyspora faeni* (53) and *Chlamydia psittaci* (54), and pure preparations of *Plasmodium berghei* (55), and hot phenol-water extracts of *Listeria monocytogenes* (56).

Recently, the clinical utility of the LAL test has been disputed. Elin (57) performed a statistical analysis of 17 different studies in humans with LAL and blood and concluded that the clinical utility of the LAL test for the diagnosis of gram-negative septicemia is marginal. Further studies by Tubbs (58) and Galloway et al. (59), respectively, showed that plasma from patients infected with *Plasmodium falciparum* and plasma from patients infected with *Borrelia recurentis* reacted positively with the LAL test.

In nearly all of the studies mentioned above, subjective methods have been used to read the LAL test, a positive test being defined as gelation or increased turbidity.

The most difficult challenge for the LAL test has been the detection of endotoxin in blood or plasma. Firstly, the concentration of circulating endotoxin in blood is usually low because of its rapid clearance in the liver. Secondly, plasma contains inhibitors of LAL, endotoxin-inactivating substances, and endotoxin-binding proteins.

Various methods have been used to extract endotoxin from plasma. The best results have been obtained by a combination of dilution and heating of the plasma (43).

Experiments with a rocket-immunoelectrophoretic method to determine the reactivity of LAL with endotoxin (43) have shown a higher degree of accuracy and sensitivity compared with several other methods, and it is suitable for diagnostic purposes.

Immunoelectrophoretic studies of the interaction between LAL and soluble antigens from *Pseudomonas aeruginosa* and *Staphylococcus aureus* have shown that LAL is highly reactive with LPS, but can react with other antigens form gram-negative and gram-positive bacteria as well (60).

LAL Testing in the Pharmaceutical Industry

The major user of the LAL test has been the pharmaceutical industry which now performs hundreds of thousands of tests annually on a variety of large and small volume parenteral fluids, biochemicals, and medical devices. The LAL test is now commonly performed for both in-process and final-release testing of many injectable fluids and invasive medical devices produced by the pharmaceutical industry all over the world.

Clinical Applications of the LAL Test

The clinical applications of the LAL test have been thoroughly discussed by Jersgensen (61). The conclusion which may be drawn from this review of the clinical applications of the LAL test is that a number of potentially successful uses have been described since the introduction of the test in the late 1960s. They have all benefited from the speed, sensitivity, and general specificity of the LAL test for bacterial endotoxin, whether it be bound endotoxin from viable gram-negative bacterial or free endotoxin as the residual evidence of prior or periodic bacterial growth. In all of these applications, the LAL test has shown to be superior in some respects to conventional methods of diagnosing bacterial endotoxins. However, none of these applications have replaced conventional methods so that LAL testing alone is used for diagnosis. Instead, the LAL test is a powerful adjunctive means of determining the presence of gram-negative bacterial in a variety of clinical cases. It has current valid diagnostic uses (meningitis, ocular infections, bacteriuria) and may eventually lead to a better understanding of other pathophysiologic consequences of endotoxin, i.e. endotoxemia.

SUMMARY OF THE INVENTION

The present inventors have now developed a novel method for determining the reaction between Limulus or Tachypleus amoebocyte lysate and endotoxin. The method shows the same sensitivity and specificity to endotoxin as the rocket-immunoelectrophoretic method (43), but it does not require highly specialized equipment or highly skilled staff to operate it so that it may be carried out in practically any clinical laboratory. It is also simpler, i.e. less time-consuming, and more economical to carry out requiring smaller amounts of amoebocyte lysate reagent. The novel method therefore presents an important economic advantage compared to the known methods.

Accordingly, the present invention relates to a method of determining the presence of an endotoxin or endotoxin-line material in a sample, which comprises a) incubating a sample with a component of horseshoe crab amoebocyte lysate or hemolymph or a synthetic analog thereof, whereby the properties of said component are altered if any endotoxin or endotoxin-like material is present in the sample so that no reaction with an antibody raised against or directed substantially only against said component or analogue or an immunological determinant thereof will take place, or so that a reaction product of a reaction of said component or analog with an endotoxin or endotoxin-like material in the sample will react with an antibody raised against or directed substantially only against said reaction product or an immunological determinant thereof.

b) reacting the incubated mixture of said sample and said component or analogue resulting from step a) with an antibody raised against or directed substantially only against said component or analog or an immunological determinant thereof whereby the antibody is bound to any of said component or analog present in the mixture, or with an antibody raised against or directed substantially only against said reaction product or an immunological determinant thereof, whereby the antibody is bound to any of said reaction product present in the mixture, and c) determining the presence of any endotoxin or endotoxin-like material in the sample by detecting any bound antibody in the reaction mixture resulting from step b), the detection of decreasing amounts of bound antibody showing the presence of an endotoxin or endotoxin-like material in the sample if the antibody is one raised against or directed substantially only against said component or analog or an immunological determinant thereof, and the detection of increasing amounts of bound antibody showing the presence of an endotoxin or endotoxin-like material in the sample if the antibody is one raised against or directed substantially only against said reaction product or an immunological determinant thereof, with the proviso that any of said component or analog or any of said reaction product present after the incubation of the sample with the component or analog in step a) is coupled to a solid support, or that said antibody is coupled to a solid support or to a bridging molecule coupled to a solid support, or that any endotoxin or endotoxin-like material present in the sample is coupled to a solid support.

In the present context, "endotoxin or endotoxin-like material" is defined as a substance which is usually a component of the outer surface of the bacterial membrane and which is usually a pyrogen, i.e. induces fever. The biologically active part of the endotoxin of gram-negative bacterial has been shown to be lipopolysaccharide, the lipid moiety (lipid A) being responsible for the pyrogenic and endotoxin properties of lipopolysaccharide. It has, however, been shown (45,46, 60) that other surface antigens may also be reactive with LAL, including surface antigens of gram-positive bacteria, and the expression is therefore intended to include any material or component from bacteria or other microorganisms such as fungi, yeasts or algae which is reactive with LAL (22,23,47,48).

The term "component of horseshoe crab amoebocyte lysate or hemolymph" is intended to include the whole lysate or hemolymph as well as the individual reactive components therein, in that the whole lysate or hemolymph comprises such reactive components reacting with endotoxin or an endotoxin-like material. A currently favored component for use in the method of the invention is a coagulogen (as present in the whole lysate). The lysate and hemolymph may be derived from all four species of horseshoe crabs, i.e. *Limulus polyphemus*, *Tachypleus tridentatus*, *Tachypleus gigas* and *Carcinoscorpius rotundicauda*, Limulus and Tachypleus lysates being currently preferred.

The term "synthetic analog" is understood to mean a substance showing the same or substantially the same reactivity with an endotoxin or endotoxin-like material as a component occurring naturally in horseshoe crab amoebocyte lysate or hemolymph. Such an analog may be prepared by chemical synthesis such as conventional peptide synthesis, preferably solid phase peptide synthesis, or by recombinant DNA techniques involving cloning a gene coding for said component into a convenient expression vector, transforming the resulting recombinant vector to a suitable microorganism, growing the organism in a suitable medium to express said gene and isolating the component thus produced from the culture medium. Specific components to be employed in the present method may be selected from a coagulation factor, e.g. Factor B, Factor C, Factor G, Factor N, pro-clotting enzyme, activated clotting enzyme, anti-LPS factor or coagulogen, and an agglutinin, e.g. a lectin such as limulin or polyphemin, the coagulation factor being typically found in the amoebocytes and the agglutinin being usually found in the hemolymph.

The term "reaction product of a reaction of said component or analog with an endotoxin or endotoxin-like material in the sample" is understood to mean any product resulting from the enzymatically catalysed cleavage or other enzymatically induced change (e.g. in the tertiary protein structure) of a substrate (including other enzymes in the enzyme cascade described above) activated by the presence of an endotoxin or endotoxin-like material in the sample in the enzyme cascade described above. The reaction product may be selected from coagulin, C-peptide, activated clotting enzyme, activated Factor B, C, G or N, or cleavage products from these factors and from pro-clotting enzyme.

The term "sample" is defined as any material to be tested for the presence of endotoxin. The term preferably includes any of the materials usually subjected to pyrogen testing. Thus, the sample may be selected from pharmaceutical preparations such as parenteral fluids or injectable fluids, i.e. preparations comprising an active substance such as a drug or a nutrient, and medical devices used for insertion into the body of a patient, e.g. invasive devices such as cannulas or catheters. Other materials commonly subjected to pyrogen testing include mitogens, biochemicals, including nutrient media and buffers, foodstuffs, drinking water and water used in the pharmaceutical industry. Furthermore, the sample may be selected from body fluids such as urine, cerebrospinal fluid, blood, serum, plasma or any product prepared from blood or lymph, thus making it possible to diagnose endotoxin-induced diseases by the method of the invention. A drawback of the known methods for detecting pyrogens in clinical samples has been that these known tests, when performed on samples of body fluids, principally plasma and serum, have not shown the specificity and sensitivity required for accurate diagnosis of bacteremia and septicemia. It has surprisingly been found that the method of the present invention may be employed for accurate detection of even minute quantities (at the picogram level) of endotoxin in plasma and serum.

In the present context, the term "immunological determinant" refers to a subsequence of said component or analog against which antibodies showing desirable properties in the test method of the invention can be raised or which will react with an antibody. Thus, the immunological determinant may for instance be a sequence spanning a cleavage site at which the component or analogue is cleaved in the enzyme cascade described above. The term "antibody" refers to a substance which is formed as a response of an animal or animal cell to exposure to said component or analog or reaction product. In order to secure an adequate specificity and sensitivity of the assay method of the invention, the antibody is preferably a monospecific antibody showing specificity towards a single component of horseshoe crab amoebocyte lysate or hemolymph rather than towards several components or whole lysate or hemolymph. For some purposes, the antibody may be a polyclonal antibody, but it is generally preferred that the antibody is a monoclonal antibody as this ensures a higher specificity and sensitivity of the assay which therefore provides a more accurate determination of endotoxin or similar materials than the conventional LAL test methods, at the same time requiring a smaller amount of the test component or analog which makes the method of the invention more economical to use.

According to the invention, the presence of an endotoxin or endotoxin-like material may be determined both negatively and positively. Negative determination results from using an antibody against said component or analog for reaction with the incubated mixture of sample and component or analog, utilizing the inability of the antibody to bind to a reaction product of the incubation of the sample with the component or analog. If little or no bound antibody is detected after the reaction, or if, at least, a significantly decreased amount of bound antibody is detected compared to an endotoxin-free control, this indicates the presence of an endotoxin or endotoxin-like material in the sample since it shows that the component or analogue has been enzymatically cleaved or otherwise structurally changed due to the presence of endotoxin so that the antibody directed against the component or analog is no longer able to bind. On the other hand, if the antibody is one directed against said reaction product, the antibody added in step b) of the method of the invention will bind in the test (or at least, increasing amounts of antibody will be bound compared to an endotoxin-free control), thus providing a positive determination of endotoxin or endotoxin-like material in the sample.

The method of the invention is suitable for both qualitative and quantitative determination of endotoxin. For quantitative measurement, the amount of antibody bound in the test may be determined by series dilutions of the samples in a manner known per se (cf. 43).

When according to the invention, any of said component or analog or any of said reaction product remaining after the incubation of the sample with the component or analog in step a) of the method above is coupled to a solid support, an antibody against the component or analog or against the reaction product may then be added to the solid support, no bound antibody, or a smaller amount of bound antibody compared to an endotoxin-free control showing, in the former case, the presence of endotoxin in the sample. In the latter case, the presence of bound antibody shows the presence of endotoxin in the sample.

Alteratively, the antibody is coupled to a solid support or to a bridging molecule coupled to a solid support, and any of said component remaining after the incubation of the sample with the component or analog in step a) of the method of the invention is bound to the antibody for further reaction with a further amount of antibody.

As a further alternative, any endotoxin or endotoxin-like material present in the sample is coupled to a solid support. It may then be incubated with the component or analogue by addition of the component or analog to the solid support followed by adding a labelled antibody either against the component or analog or against the reaction product resulting from the incubation of the component or analog with the sample. In this case, the component (or analog) should be the whole lysate or hemolymph or the compound in the lysate with which the endotoxin reacts to induce the enzyme cascade described above.

In another aspect, the present invention relates to a monoclonal antibody for use in the method of the invention, the antibody being raised against or directed substantially only against a component of horseshoe crab amoebocyte lysate or hemolymph or a synthetic analog thereof, or an immunological determinant thereof.

In a further aspect, the present invention relates to a test kit for determining the presence of an endotoxin or endotoxin-like material in a sample, the kit comprising a) an antibody raised against or directed substantially only against a component of horseshoe crab amoebocyte lysate or hemolymph or a synthetic analog thereof, or an immunological determinant thereof, or an antibody raised against or directed substantially only against a reaction product of a reaction of said component or analog with an endotoxin or endotoxin-like material or an immunological determinant thereof, and b) a component of horseshoe crab amoebocyte lysate or hemolymph or a synthetic analog thereof.

DETAILED DISCLOSURE OF THE INVENTION

As indicated above, the antibody binding with said component or analog or binding with said reaction product is preferably a monospecific antibody against a specific component in horseshoe crab amoebocyte lysate or hemoloymph (or a synthetic analog thereof). The monospecific antibody may be prepared by injecting a suitable animal with a substantially pure preparation of the component or analog in question followed by one or more booster injections at suitable intervals (e.g. two weeks to a month) up to six months before the first bleeding. Then, while continuing this established immunization regimen, the animals are bled about one week after each booster immunization, and antibody is isolated from the serum in a conventional manner, e.g. as described in Harboe and Ingild, Scan. J. Immun. 2 (Suppl. 1), 1973, pp. 161–164.

For purposes not requiring a high specificity, the antibody may be a polyclonal antibody. Polyclonal antibodies may be obtained substantially as described in Harboe and Ingild, op. cit. In most cases, however, it is preferred that the antibody used in the method of the invention is a monoclonal antibody as this generally provides a higher specificity and accuracy of the assay, at the same time requiring less time to perform. Furthermore, a mixture of two or more different monoclonal antibodies may be employed as this may increase the detection limit and sensitivity of the test. The monoclonal antibody may be obtained by the method described below.

The antibody used in the present method is preferably in substantially pure form to improve the accuracy of the assay.

In some cases, such as when the antibody is coupled to solid particles (as explained below) which agglutinate when the antibody reacts with the substance against which it is directed (i.e. the component, analog or reaction product), the antibody may be used in unmodified form. However, for most purposes the antibody is preferably provided with a label for the detection of bound antibody or, alternatively (such as in a double antibody assay), a combination of labelled and unlabelled antibody may be employed. The substance used as label may be selected form any substance which is in itself detectable or which may be reacted with another substance to produce a detectable end product. Thus, the label may be selected from enzymes, fluorescent or chemiluminescent substances, chromophores, radioactive isotopes and complexing agents.

Examples of enzymes useful as labels are peroxidases (e.g. horseradish peroxidase), phosphatases (e.g. acid phosphatase), β-galactosidase, urease, glucose oxidase, carbonic anhydrase, acetylcholinesterase, glucoamylase, lysozyme, malate dehydrogenase, glucose-6-phosphate dehydrogenase and ribonuclease.

Enzymes are not in themselves detectable, but must be combined with a substrate to catalyse a reaction the end product of which is detectable. Thus, a substrate may be added to the reaction mixture resulting from step b) above resulting in a colored, fluorescent or chemiluminescent product or in a color change or in a change in the intensity of the color, fluorescence or chemiluminescence. Examples of substrates which are useful in the present method as substrates for the enzymes mentioned above are $H_2O_2$, p-nitrophenylphosphate, lactose, urea, β-D-glucose, $CO_2$, choline ester, starch, M. lysodeikticus, malate, clucose-6-phosphate and RNA. The substrate may be combined with, e.g. a chromophore which is either a donor or acceptor.

Fluorescent substances which may be used as labels for the direct detection of bound antibody may be selected from 4-methylumbelliferyl-D-galactopyranoside, 4-methylumbelliferyl-phosphate and 3-(p-hydroxyphenyl) propionic acid. These substances are in themselves detectable by means of a fluorescence spectrophotometer, permitting both qualitative and quantitative measurement of fluorescence.

Chemiluminescent substances which may be used as labels for the direct detection of antibody bidning may be selected from isoluminol-/EDTA/$H_2O_2$, peroxidate/eosin/EDTA and luciferase and a substrate therefor. These substances are in themselves detectable by means of a spectrophotometer, permitting qualitative as well as quantitative measurement of chemiluminescence.

Chromophores which may be used for the direct detection of bound antibody may be selected from 5-aminosalicylic acid, 2,2'-azino-di-(3-ethylbenzthiazoline-6-sulfonic acid, o-phenylenediamine, o-diaminicidine, 3-methyl-2-benzothiazoline hydrazone, 3-(dimethylamino)-benzoic acid, o-toluidine, 3,3',5,5'-tetramethylbenzidine, o-nitrophenyl-β-D-galactoside and p-nitrophenyl phosphate. These substances may in themselves be detected by means of a spectrophotmeter and used for the quantitative as well as qualitative determination of color, for instance color intensity or color change.

Radioactive isotopes which may be used for the direct detection of bound antibody may be selected from $^{125}I$, $^{3}H$, $^{35}P$, $^{131}I$ and $^{14}C$. The radioactivity emitted by the isotopes may be measured in a γ-counter or a scintillation counter, permitting qualitative and quantitative measurement of bound radioactivity.

Complexing agents which may be employed for the detection of bound antibody may be selected from biotin (which forms a complex with avidin and streptavidin), Protein A (which forms a complex with immunoglobulins) and lectin (which forms a complex with carbohydrate determinants, e.g. receptors). In this case, the complex is not in itself directly detectable, necessitating labelling of the substance with which the complexing agent forms a complex. The marking may be performed with any of the substances indicated above for the labelling of the antibody, i.e. by means of a fluorescent or chemiluminescent substance, a chromophore, an anzyme or a radioactive substance.

When, in the method of the invention, the antibody is coupled to a bridging molecule coupled to a solid support, the bridging molecule which serves as a link between the solid support and the antibody may be selected from glutaraldehyde, carbodiimide, lysine, Protein A and hydrazide. The antibody may either be labelled or unlabeled, and in one embodiment of the method, unlabelled antibody may be coupled to a solid support followed by sequential addition of the incubated mixture of the component or analog and the sample and labelled antibody.

The solid support employed in the method of the invention preferably comprises a polymer. The support may in itself be composed of the polymer or may comprise a matrix coated with the polymer. The matrix may be of any solid material suited for the present purpose such as glass, paper or plastic. The polymer which may either in itself comprise the solid support or which is applied on a matrix may be selected from a plastic, cellulose such as nitrocellulose paper, cyanogenbromide-activated paper, 1-(3-nitrobenzyloxymethyl)pyridium chlorride paper diazobenzyloxymethyl paper, nitrobenzyloxymethyl paper or aminobenzyloxymethyl paper, a silicone polymer and silica or a silicate. Examples of suitable plastics are latex, a polystyrene, polyvinylchloride, polyurethane, polyacrylamide, polyvinylacetate and any suitable copolymer thereof. Examples of silicone polymers include siloxane; examples of silicates include glass. The polymer may optionally be provided with functional groups to facilitate binding of a particular reagent forming part of the enzyme cascade explained above, examples of such groups being the bridging molecules mentioned above, optionally coupled to a solid support.

The physical shape of the solid support is not particularly critical, although some shapes may be more convenient to use than others for specific purposes. Thus, the solid support may be in the form of a plate, e.g. a thin layer or, preferably, microtiter plate, strip, film solid particles, including Protein A-coated bacteria, or paper. Solid particles for use in the present method typically have a size in the range of about 1–10 μm.

DESCRIPTION OF PREFERRED EMBODIMENTS

In one embodiment, the method of the invention comprises a) coupling an antibody raised against or directed substantially only against coagulogen or an immunological determinant thereof, or raised against or directed substantially only against coagulin or C-peptide or an immunological determinant thereof, to a solid support or to a bridging molecule coupled to a solid support, b) incubating a sample with a coagulogen-containing material so as to cleave coagulogen to coagulin and C-peptide if an endotoxin or endotoxin-like material is present in the sample, c) adding the incubated mixture resulting from step b) to the solid support so as to bind any coagulogen present in the sample if the antibody coupled to the solid support is one raised against or directed substantially only against coagulogen or an immunological determinant thereof, or so as to bind any coagulin or C-peptide present in the sample if the antibody coupled to the solid support is one raised against or directed substantially only against coagulin or C-peptide or an immunological determinant thereof, d) adding to the solid support a labelled antibody raised against or directed substantially only against coagulogen or an immunological determinant thereof, so as to bind to any bound coagulogen present on the solid support, or raised against or directed substantially only against coagulin or C-peptide or an immunological determinant thereof, so as to bind to any bound coagulogen or to any bound coagulin or C-peptide present on the solid support, and e) determining the presence of any endotoxin or endotoxin-like material in the sample by detecting any labelled antibody bound to the solid support of step d), the detection of decreasing amounts of bound antibody showing the presence of an endotoxin or endotoxin-like material in the sample if the antibody is one raised against or directed substantially only against coagulogen or an immunological determinant thereof, and the detection of increasing amounts of bound antibody showing the presence of an endotoxin or endotoxin-like material in the sample if the antibody is one raised against or directed substantially only against coagulin or C-peptide or an immunological determinant thereof.

In another embodiment, the method of the invention comprises a) incubating a sample with a coagulogen-containing material so as to cleave the coagulogen to coagulin and C-peptide if any endotoxin or endotoxin-like material is present in the sample, b) the incubated mixture of step a) is added to a solid support to bind any coagulogen present in the mixture or to bind any coagulin or C-peptide present in the mixture, c) adding to the solid support a labelled antibody raised against or directed substantially only against coagulogen or an immunological determinant thereof to bind to any coagulogen bound to the solid support, or raised against or directed substantially only against coagulin or C-peptide or an immunological determinant thereof to bind to any coagulin or C-peptide bound to the solid support, and d) determining the presence of any endotoxin or endotoxin-like material in the sample by detecting the presence of any labelled antibody bound to the solid support of step c), the detection of decreasing amounts of bound antibody showing the presence of an endotoxin or endotoxin-like material in the sample if the antibody is one raised against or directed substantially only against coagulogen or an immunological determinant thereof, and the detection of increasing amounts of bound antibody showing the presence of an endotoxin or endotoxin-like material in the sample if the antibody is one raised against or directed substantially only against coagulin or C-peptide or an immunological determinant thereof.

In both these embodiments, it may be an advantage to wash the solid support at least once, and possibly up to several times, after the reaction of the incubated mixture with the antibody in order to remove unbound antibody (it should be noted that the two embodiments summarized above closely correspond to direct and double enzyme linked immunosorbent assay (ELISA), respectively). These ELISA methods are particularly advantageous as they have been found to require 40 times less of the specific component employed (i.e. coagulogen present in LAL) than the conventional gel clot test. Furthermore, the time needed to perform the test is about 4 hours for several hundred tests, presenting an important improvement over the known test methods. Apart from these advantages, the results obtained with clinical samples, especially blood or plasma, by the present method are not impaired by the presence of interfering substances in blood so that the method may be used to test all clinical samples. The ELISA method is well established and may be carried out with existing laboratory equipment and may also be subjected to automation. The present method therefore has wide applicability in clinical laboratories for diagnostic purposes and in the pharmaceutical industry as an assay for contaminants in raw materials or pharmaceutical preparations.

In a further embodiment, the method of the invention comprises a) coupling an antibody raised against or directed substantially only against colagulogen or an immunological determinant thereof, or raised against or directed substantially only against coagulin or C-peptide or an immunological determinant thereof, to the surface of solid particles, b) incubating a sample with a coagulogen-containing material so as to cleave the coagulogen to coagulin and C-peptide if any endotoxin or endotoxin-like material is present in the sample, c) adding the incubated mixture of step b) to the antibody of step a) so as to cause agglutination of the solid particles in the presence of coagulogen when the antibody is one raised against or directed substantially only against coagulogen or an immunological determinant thereof, or so as to cause agglutination of the solid particles in the presence of coagulin or C-peptide when the antibody is one raised against or directed substantially only against coagulin or C-peptide or an immunological determinant thereof, and d) determining the presence of an endotoxin or endotoxin-like material in the sample by the absence of agglutination of solid particles to which an antibody raised against or directed substantially only against coagulogen or an immunological determinant thereof is coupled, or by agglutination of the solid particles to which an antibody raised against or directed substantially only against coagulin or C-peptide or an immunological determinant thereof is coupled.

In this embodiment, the presence of endotoxin may be detected directly (visually) be determining the agglutination of the solid particles to which antibody is bound. In other words, no labelling of the antibody will usually be needed in this embodiment of the present method.

The monoclonal antibody of the invention, which has been found to be particularly advantageous to employ in the present method for the reasons stated above, may show the features described above for antibodies in general. It may be prepared by a method comprising a) immunizing a suitable animal or a suitable animal cell with an antigen consisting essentially of a component of horseshoe crab amoebocyte lysate or hemolymph or a synthetic anolog thereof, or an immunological determinant thereof, or consisting essentially of a reaction product of a reaction of said component or analog with an endotoxin or endotoxin-like material, or an immunological determinant thereof, to obtain cells producing an antibody to said antigen.

b) fusing cells producing the antibody to said antigen with myeloma cells of a suitable cell line, c) selecting and cloning the resulting hybridoma cells producing said antibody, d) growing the hybridoma cells in a suitable medium to produce said antibody, and e) recovering the resulting antibody from the culture.

The immunization of the animal is preferably carried out by means of a solution of said component, analog or reaction product in a suitable solvent such as an aqueous buffer, e.g. phosphate buffered saline or an adjuvant. Examples of suitable adjuvants are Freund's complete or incomplete adjuvant and aluminium hydroxide. Suitable animals for immunization purposes may be selected from rabbits, goats, horses, sheep, mice, chickens and guinea pigs. The bleeding of the animal and isolation of the (polyclonal) antibody may be performed in a manner known per se.

The antibody-producing cells used for fusions with the myeloma cells are preferably spleen cells or lymph node cells. The myeloma cells and antibody-producing cells need not be derived from the same animal species provided that it is possible to fuse cells from one species with cells from another, e.g. mouse cells with rat cells, rat cells with human cells, or mouse cells with human cells. It is, however, preferred to use the same animal species as the source of both myeloma and antibody-producing cells. One preferred hybridoma cell line for the practice of the present invention may be constructed by fusing a mouse myeloma cell with an antigen-primed mouse spleen cell.

Cell fusions may be carried out according to a modification of the method disclosed by Köhler and Milstein, *Nature* 256, 1975, p. 495. Thus, the fusion of the cells producing the antibody with the myeloma cells is preferably performed in the presence of a fusion promoter such as polyethylene glycol. A ratio of about 10 antibody-producing cells permyeloma cell is preferred. The myeloma cell line employed is preferably of the so-called drug resistant type so that, in a selective medium, unfused myeloma cells die while fused, hybrid cells survived. In conventional practice, cell lines which are resistant to 8-azaguanine lacking the enzyme hypoxanthine-guanine phosphoriboxyltransferase and therefore unable to grow in HAT medium (containing hypoxanthine, aminopterin and thymidine), are most frequently used for cell fusions. Furthermore, the myeloma cell line should preferably be of the "non-secreting" type which means that it does not in itself form antibodies or heavy or light immunoglobulin chains.

Hybridoma cells producing the antibody against said component, analogue or reaction product may be selected by culturing unfused antibody-producing cells, unfused myeloma cells and fused cells in individual vessels and in a selective medium in which the unfused myeloma cells do not divide so that they die after about 1–2 weeks. The unfused antibody-producing cells only live through a limited number of cell division cycles after which they also die (1–2 weeks), whereas successfully fused cells continue to divide because they have inherited permanent growth properties from the parent myeloma cells and the ability to synthesize the enzyme hypoxanthine phosphoribosyltransferase from the parent antibody-producing cells so that they are able to grow in the selective medium (in casu HAT medium).

It should be noted that monoclonal antibodies produced by the fused cells which have been raised against the same antigen may nevertheless be distinct from each other dependent on the specific determinant inducing their formation. However, for any given hybridoma clone, all antibodies produced by the clone are monospecific for a particular determinant in the antigen molecule. Hybridomas producing the desired antibody may be selected, e.g. by limiting dilution or another suitable method, and cloned by repeated recloning, e.g. using a limiting dilution system in a manner known per se, and cloned monoclonal antibodies of a high purity may be obtained by culturing the hybridoma cells in a suitable medium, e.g. Dulbecco's minimal essential medium. By this in vitro technique, monoclonal antibodies are produced which are only contaminated with minor amounts of proteins from the heterologous serum, for instance fetal calf serum, present in the growth medium.

In order to produce a significantly higher concentration of monoclonal antibodies with a purity which is only slightly reduced compared to that of the in vitro produced antibodies, the selected hybridoma cells may also be grown in a body cavity of an animal. According to this method, the desired hybridoma clone is injected into an animal such as a mouse, preferably a syngeneic or semisyngeneic mouse, resulting in the formation of an ascites tumor which releases high concentrations of the antibody (about 2–10 mg/ml) in the blood and ascites fluid of the animal. Even though the animals also produce normal immunoglobulins, these will only amount to about 5% of the monoclonal antibodies.

As the monoclonal antibodies of the invention are typically secreted from the cells, they may be recovered from the cell supernatant or body fluid by standard procedures for isolating extracellular products, including centrifugation, filtration, precipitation, extraction and/or chromatography.

The individual reagents a) and b) of the test kit according to the invention may exhibit any of the features described above for the antibody and component of horseshoe crab amoebocyte lysate, respectively. Apart from this, the kit may be one which comprises both labelled and unlabelled antibody (in particular for use in a double antibody assay). Other ingredients in the kit of the invention may be an endotoxin standard which is useful for quantitative assays in particular, making it possible to determine higher or lower levels of antibody binding compared to the standard control, as well as pyrogen-free water (in order to avoid erroneous results of the test resulting from the use of pyrogen-contaminated water) for diluting the reagents employed in the test kit and method of the invention.

The test kit of the invention may be employed for the diagnosis of clinical/pathological conditions resulting from infections by a wide variety of pathogens, including gram-negative bacteria (e.g. Enterobacteriaceae, e.g. *E. coli, Shigella dysenteriae*, Pseudomonas spp., Salmonella spp., Neisseria spp., Clostridium spp., *Vibrio cholerae*, Pasteurella spp.) and gram-positive bacteria (e.g. *Listeria monocytogenes* and Streptococcus spp.); Mycoplasma spp.; Chlamydia spp.; *Treponema pallidum*; fungi (e.g. *Candida albicans*) and protozoans such as the malaria parasite *Plasmodium falsiparum*. The kit is also useful for detecting contamination of pharmaceutical raw materials and preparations and medical devices either by these pathogens as such or by residual pyrogenic endotoxins or other surface antigens derived from the pathogens.

FIG. or is a standard curve of LAL-ELISA which shows that the residual coagulogen measured by an ELISA test is conversely proportional to the concentration of endotoxin.

FIGS. 3–6 show LAL-endotoxin reaction curves resulting from different combinations of incubation times and dilutions of LAL.

Figure 7:
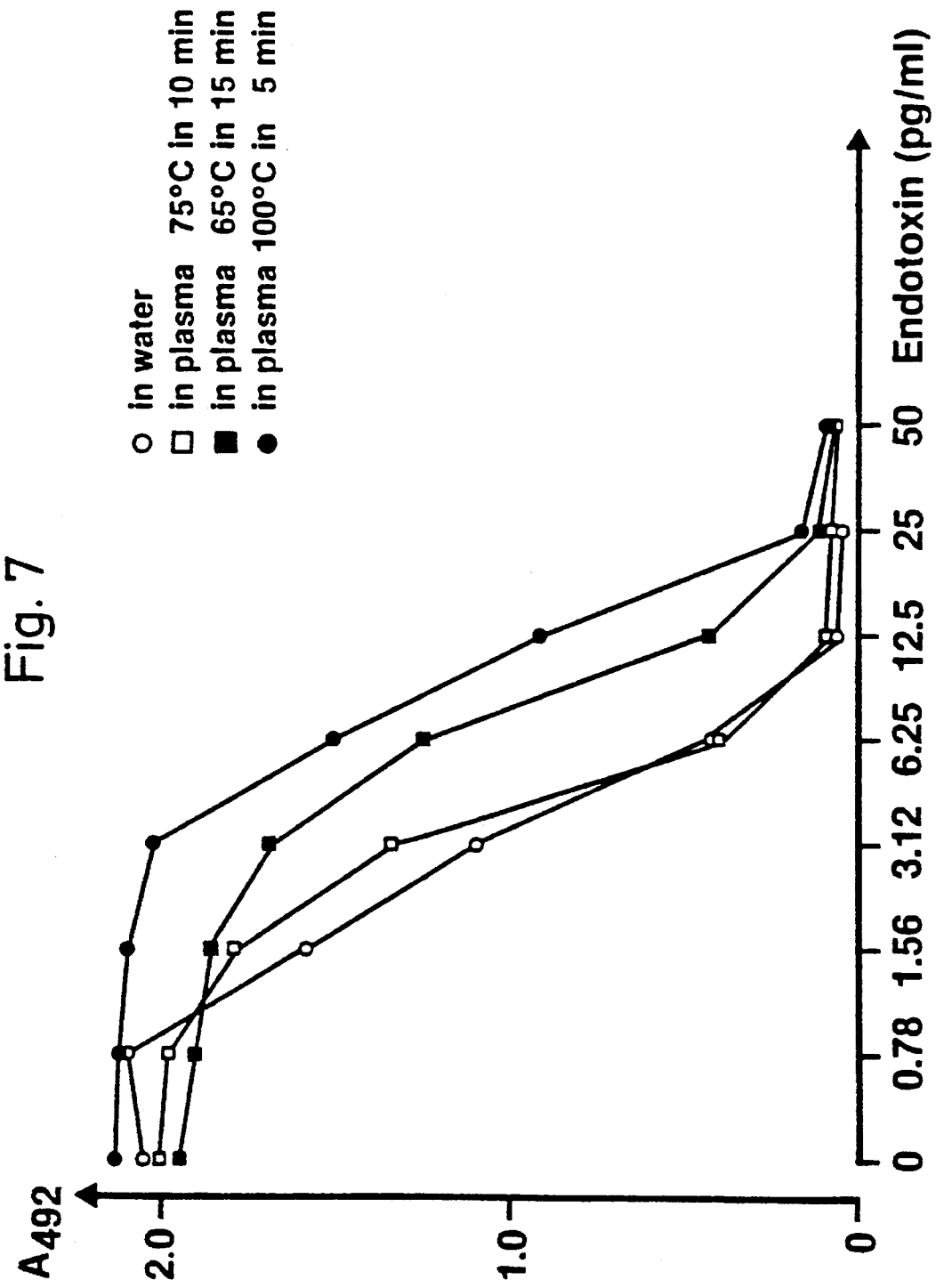

FIG. 7 shows that the treatment of plasma with 10-fold dilution and subsequent 10 minutes of incubation at 75° C. yielded almost 100% recovery of endotoxin while only about 50% was achieved by the other two treatments.

Figure 8:
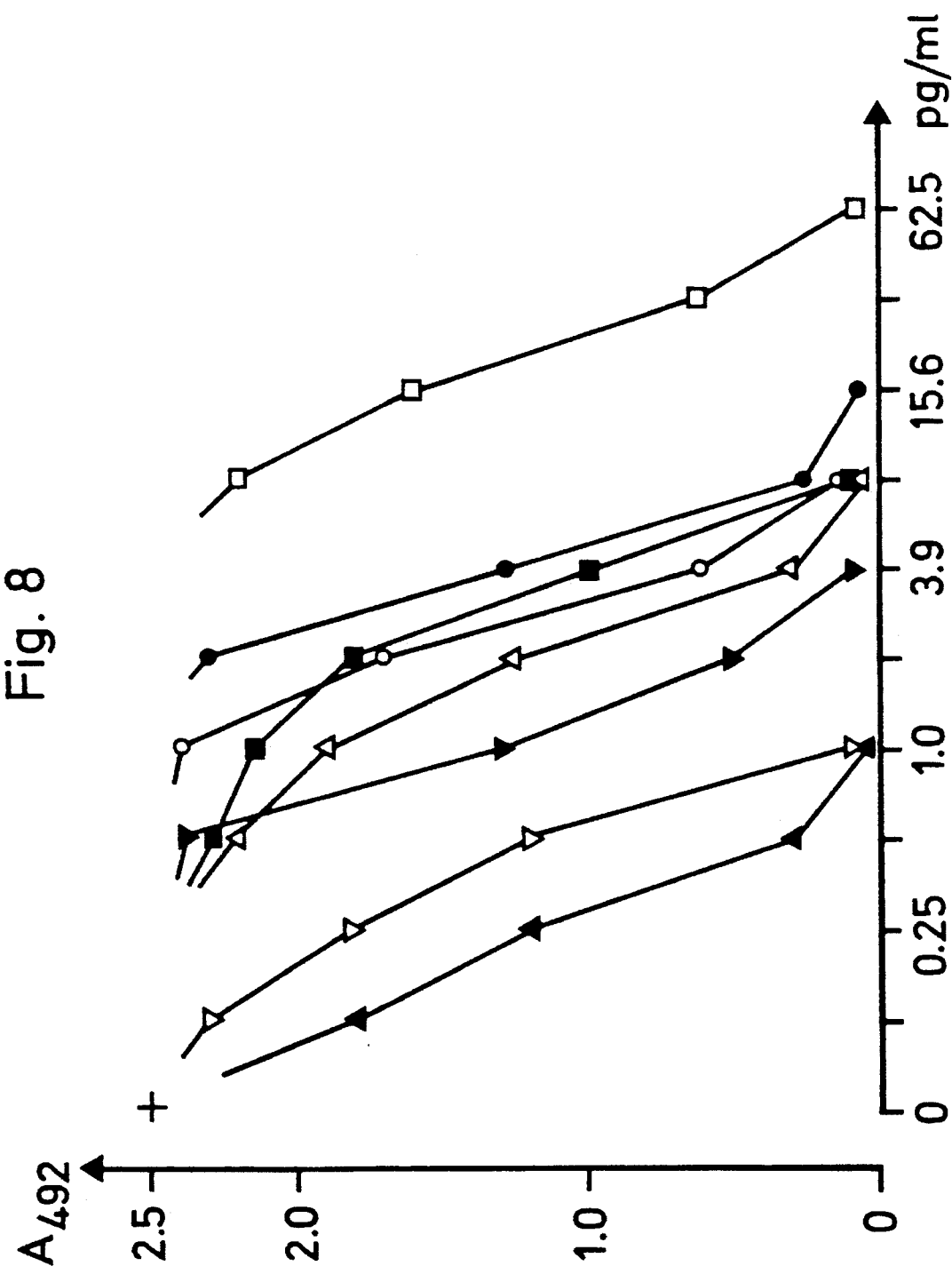
Figure 9:
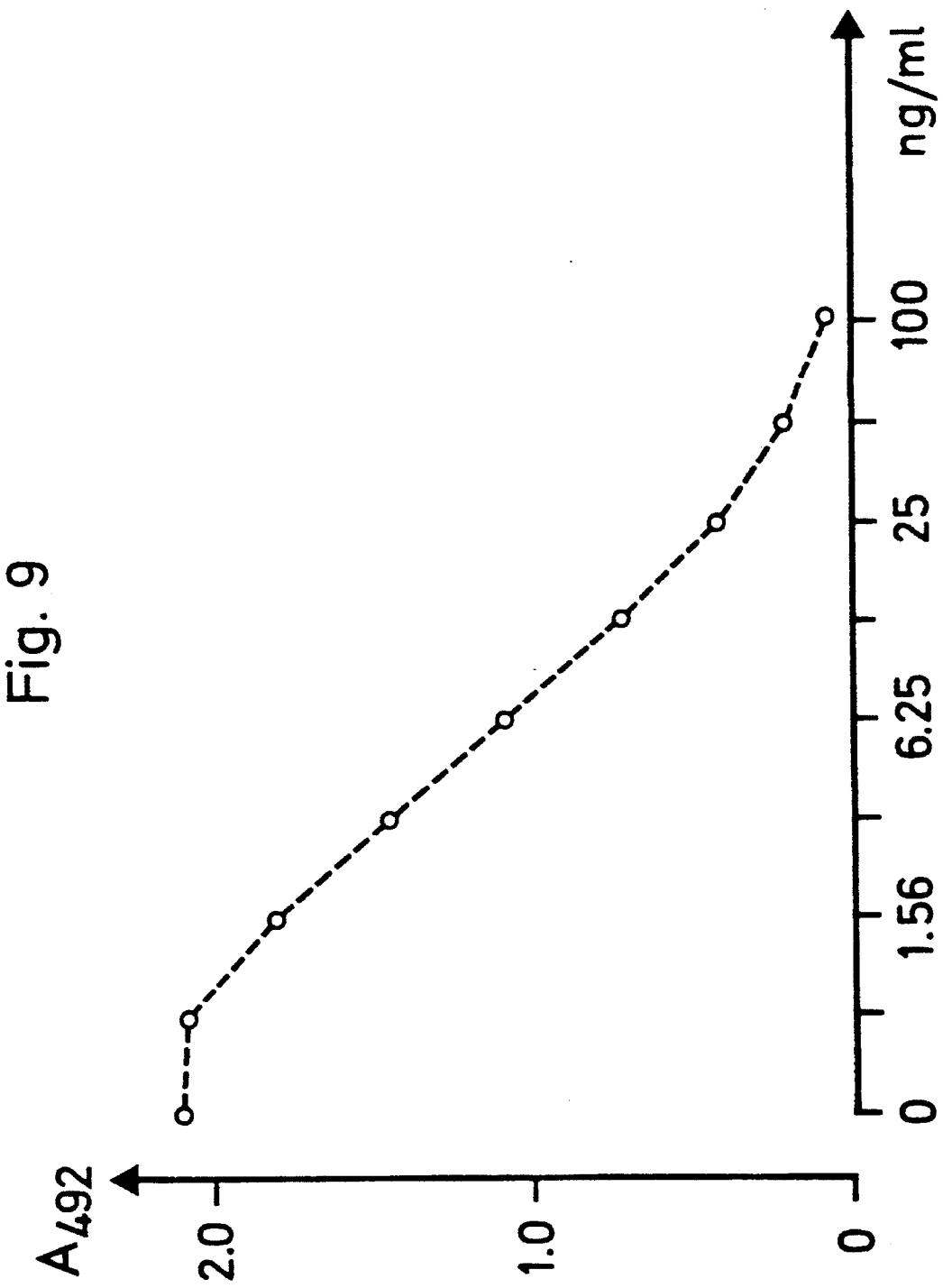

FIGS. 8 and 9 show curves of the LAL-ELISA of 8 LPS from various strains of gram-negative bacteria (FIG. 8) and (1–3)-β-D-glucan (FIG. 9). The LPS used were *Salmonella enteritidis* (▲), *E. coli* J5 (▽), *Pseudomonas aeruginosa* (▼), *Salmonella abortus* equi (△), *E. coli* O55:B5 (o), *Salmonella typhimurium* (■), *E. coli* O111:B4 (●) and *Salmonella minnesota* (□). The symbol (+) in FIG. 8 positions the value of absorbance of LAL obtained in endotoxin-free water.

Figure 10:
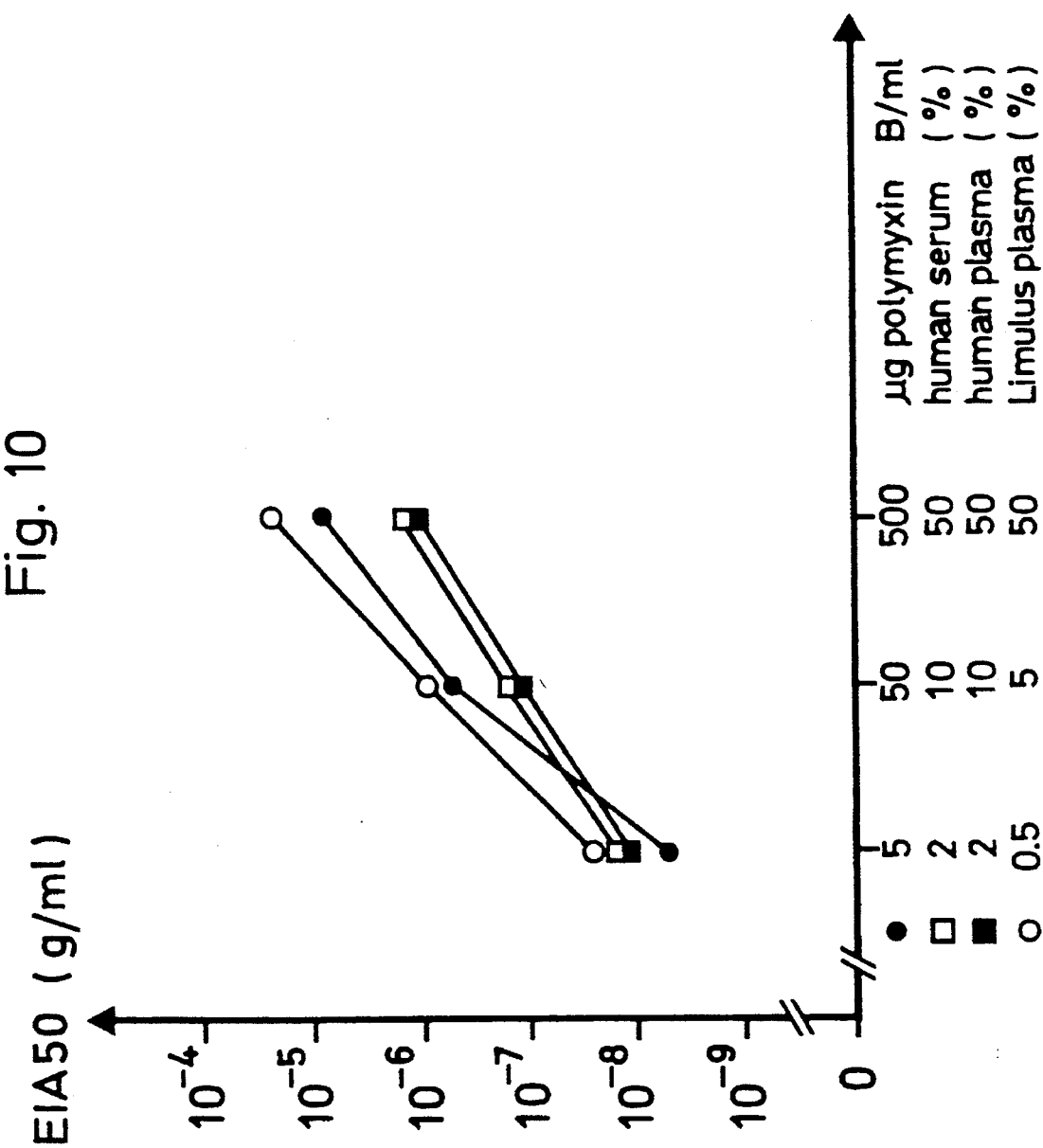

FIG. 10 shows the effect of dilution on EIA50 of human serum (□), human plasma (■), polymyxin B (●) and Limulus plasma (o). Human serum and plasma were prepared from one volunteer. Limulus plasma was the cell-free supernatant prepared by centrifuging the pooled blood of twelve *Limulus polyphemus* at 5000×g for 30 minutes.

The invention is further illustrated by the following non-limiting Examples.

EXAMPLE 1

Preparation of monoclonal antibody against coagulogen (LAL)

1. Preparation and purification of coagulogen

A Limulus amoebocyte lysate (LAL) was produced from *Limulus polyphemus* by conventional methods as disclosed in Tvede M, and Bak L, *Acta Pathol. Microbiol. Immunol. Scand.*Sec. B 91, 1983, pp. 9–15.

10ml of lysate were dialyzed and mixed with an equal volume of 0.05M Tris-HCl buffer, pH 7.9, containing 2 mM $cacl_2$. The mixture was applied to a DEAE-Sepharose® CL-6B coluna (15×1.5 cm) equilibrated with the same buffer. The fraction which was not adsorbed to the column was further applied to a Heparin-Sepharose® CL-6B column equilibrated with the same Tris buffer. Coagulagen was bound to the Heparin-Sepharose® column under these conditions, but could be eluted with a 0.05M Tris-HCl buffer, pH 7.9, containing 0.15M NaCl and 2 mM $CaCl_2$. The eluted material contained>90% pure coagulogen as determined by SDS-polyacrylamide gel electrophoresis.

2. Immunization of Balb/c mice with coagulogen

Purified coagulogen as obtained in step 1 above was adsorbed to aluminium hydroxide gel ($Al(OH)_3$) corresponding to 200 μg of coagulogen/mg $Al(OH)_3$, and the suspension was adjusted to 1 mg of $Al(OH)_3$/ml.

For the primary immunization, each mouse was injected intraperitoneally with 0.5 ml of coagulogen suspension emulsified with 0.5 ml of Freund's incomplete adjuvant (corresponding to 100 μg of coagulogen/mouse). Two weeks later, each mouse received an intraperitoneal booster injection of 0.5 ml of coagulogen suspension without any Freund's adjuvant.

A similar dose was injected on day 28, and 4 days later the spleen was removed and a spleen cell suspension was prepared by carefully dissecting and disrupting the spleen. The resulting spleen cells were used for cell fusions in the following step.

3. Cell fusion and culture of cells

The spleen cells obtained above were mixed with myeloma cells (X63Ag8.653) in a ratio of 10:1 ($10^8$ spleen cells to $10^7$ myeloma cells) and incubated with a polyethylene glycol solution (50% w/v PEG 1500, 7% w/v DMSO (dimethylsulphoxide) in phosphate buffered saline) for 90 seconds at 37° C. to promote cell fusion. 20 ml of Dulbecco's minimal essential medium (DMEM) were added, and the cells were centrifuged at 1,000×g. The cell pellet was resuspended in 100 ml of HAT medium (containing hypoxanthine, aminopterin and thymidine) containing 10% foetal calf serum, and the cells were distributed in 10 96-well microtiter plates (NUNC, Denmark). $10^4$ cells/well from normal mice had been added to each well as feeder cells to promote cell growth and inhibit microbial contamination. The medium was changed twice a week.

4. Selection of hybridoma cells producing an anti-coagulogen antibody

Positive clones wee screened by means of an enzyme-linked immunosorbent assay (ELISA). 96-well microtiter plates (Immunoplates, NUNC, Denmark) were coated with coagulogen which had been purified as described above. The coagulogen was diluted in a carbonate buffer, pH 9.0, to 2 μg/ml, and 100 μl of the coagulogen-containing buffer were added to each well. After incubation overnight at 4° C., the wells were washed four times with phosphate buffered saline (PBS) containing 0.05% Tween® 20.

The wells were incubated for one hour with 100 μl of culture supernatant from the cell fusion plates prepared in step 3, diluted 1:10 in PBS containing 0.02% Tween® 20, washed and incubated for one hour with peroxidase-conjugated rabbit anti-mouse Ig (Dakopatts, Copenhagen, code P260, diluted 1:1000). The peroxidase was reacted with 5 μl of a 35% $H_2O_2$ in 10 ml of a citrate-phosphate buffer (7.3 g of citric acid.$H_2O$ and 11.86 g of $Na_2HPO_4.2H_2O$ per 1000 ml of distilled water), pH 5.0 containing 8 mg of orthophenylene diamine. The reaction was stopped with 1M $H_2SO_4$, and the absorbance was read at 492 nm.

After cultivation for 2 weeks, hybridoma supernatants from 17 wells showed a strong positive reaction. Hybridoma cells from 10 of these wells were selected and cloned and recloned by limiting dilutions. 7 stable clones were established. The resulting hybridoma cell clones were grown in cell culture flasks in DMEM medium supplemented with 10% foetal calf serum at 37° C., 5% $CO_2$ and 90% humidity as well as injected ($10^7$ cells) into Pristane-treated mice (mice injected intraperitoneally two weeks earlier with 1 ml of Pristane), which, after a certain incubation time, leads to the formation of a tumor in the mouse, releasing high concentrations of antibody (2–3 mg/ml) in its blood and ascites.

5. Purification of monoclonal antibodies

Culture supernatants were concentrated on a Millipore ultrafiltration system. NaCl was added to 3.3M, glycine to 1.65M, and the pH was adjusted to 8.85 with 0.2M NaOH. Antibodies were then passed through a protein A column. Bound antibodies were eluted with 0.1M citrate-phosphate, pH 2.8. The pH was adjusted to 8.0 with Tris-Hcl. The amount of antibody was measured on a spectrophotometer as $A_{280}$, assuming $A_{280}/1\%=14$. For a more precise determination, an ELISA method was used which only measured mouse antibody. Microtiter plates were coated with rabbit anti-mouse immunoglobulin (Dakopatts, code 2109) diluted 1:500 in PBS. Dilution series of a known mouse Ig standard (20 µg of mouse Ig/ml) and dilutions of unknown samples were added. Bound mouse Ig was detected with a peroxidase-conjugated rabbit anti-mouse Ig (Dakopatts code P260) diluted 1:1000. From a standard curve, unknown concentrations of mouse Ig could be calculated.

Antibody from ascites fluid was purified in a essentially the same way. However, the ascites fluid was diluted 1:1 with a NaCl/glycine/NaOH buffer as described above before it was applied to the protein A column.

6. Characterization of the monoclonal antibodies

The classes and subclasses of the monoclonal antibodies produced by the hybridoma cells were tested in an ELISA method with biotin-labelled class/subclass specific rabbit antibodies against mouse Ig (Zymed Corporation, USA). The method was essentially the same as described above for measurements of amounts of mouse Ig, except that detecting antibody was biotin-labelled rabbit antibody against mouse IgG1, IgG2a, IgG2b, IgG3, IgM or IgA. Binding was finally detected with peroxidase-labelled streptavidin. All antibodies were of the IgG1 subclass and had K light chains.

EXAMPLE 2

Reactivity of the monoclonal antibodies with coagulogen in Limulus amoebocyte lysate and lack of reactivity with endotoxin-reacted Limulus amoebocyte lysate 3 µl of each of Limulus amoebocyte lysate (LAL) and lipopolysaccharide (LPS) reacted LAL were applied to an (1%) agarose gel and subjected to electrophoresis for two hours at 20 V/cm. After electrophoresis, a piece of nitrocellulose paper was placed on top of the agarose gel, and a pressure of 5 kg was maintained for about 20 minutes to bind proteins in the agarose gel to the nitrocellulose paper. Excess binding sites on the nitrocellulose paper were blocked with 0.05% Tween® 20.

Figure 1:
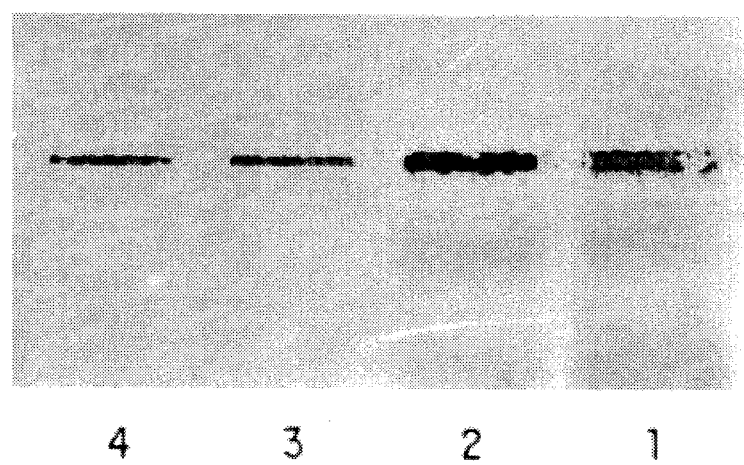
FIG. 1 shows that the band of coagulogen disappears after the reaction of Limulus amoebocyte lysate with endotoxin, indicating the loss of the reactivity of coagulogen with the antibody.

The nitrocellulose paper was then incubated with a monoclonal antibody produced as described in Example 1. 200 µl of culture supernatant containing the antibody were added to 50 ml of PBS containing 0.2% Tween® 20. After incubation overnight, an enzyme-labelled secondary antibody (peroxidase-conjugated rabbit anti-mouse, Dakopatts, Copenhagen) diluted to 1:1000, was added. Finally, tetramethylbenzidine and $H_2O_2$ were added (tetramethylbenzidine (24 mg) is dissolved with 80 mg of dioctyl sodium sulfasuccinate in 10 ml of ethanol and added to 30 ml of citrate-phosphate buffer, pH 5.0, and 20 µl of 30% $H_2O_2$ are added. Distilled water is added to 50 ml). Bound antibody was visualized as strongly blue staining. It appears from FIG. 1 that the monoclonal antibody reacts with coagulogen in non-reacted LAL, but not with LPS-reacted LAL. The immunoblotting method employed was otherwise as disclosed in C. Koch et al., *J. Immunological Methods* 84, 1985, pp. 271–278.

EXAMPLE 3

Detection of endotoxin in an enzyme-linked immunosorbent assay (ELISA)

10 µl of a commercial LAL preparation (purchased from the Association of Cape Cod, Woodshole, Mass. USA) which had been reconstituted and diluted 1:4 in a pyrogen-free Tris-$Mg^{++}$ buffer, were added to each of a number of small glass test tubes. To each tube were added 10 µl of a test sample comprising varying concentrations (cf. FIG. 2) of USP reference standard endotoxin [*E. coli* 055:B5, Whittaker M. A. Bioproducts, Inc., Walkersville, USA] (including a negative control which is an endotoxin-free buffer). The mixture was incubated at 37° C. for one hour. The reaction was stopped by adding 0.5 ml of carbonate buffer, pH 9.6 (containing 1.59 g of $Na_2CO_3$ and 2.93 g of $NaHCO_3$ per 1000 ml of distilled water) to each tube. 1:50 dilutions were made from each tube in the carbonate buffer.

100 µl of the diluted incubated mixture were added to each well of a 96-well microtiter plate (NUNC, Denmark). After incubation for one hour at room temperature, the plates were washed four times with PBS (containing 29.2 g of NaCl, 0.2 g of KCl, 0.2 g of $KH_2PO_4$, 1.15 g of $Na_2HPO_4.2H_2O$ and 10 ml of Triton® X per 1000 ml of distilled water). Horseradish peroxidase was conjugated with a monoclonal anti-coagulagen antibody prepared as described in Example 1 by the periodate method essentially as described by Wilson and Nakane (62). Thus, 4 mg of HRP dissolved in 1 ml of distilled water were mixed with 0.1 ml of freshly made 100 mM $NaIO_4$ and stirred for 30 minutes at room temperature. This solution was dialyzed overnight at 4° C. against 1 mM sodium acetate buffer (pH 4.4) and then mixed with 8 mg of monoclonal antibody (dissolved in 1 ml of 50 mM carbonate buffer, pH 9.5). After stirring for 2 hours at room temperature, 0.1 ml of fresh $NaBH_4$ solution (4 mg/ml) was added and incubated at 4° C. for 2 hours. The resulting conjugate was dialyzed against phosphate-buffered saline (PBS, pH 7.3) at 4° C. overnight. It was then added to an equal volume of glycerol (87%) and stored at −20° C. 100 µl of the peroxidase-conjugated monoclonal antibody diluted 1:20,000 in dilution buffer (10 g of bovine serum albumin in 1000 ml of washing buffer, pH 7.2) was added to the wells and incubated for one hour. After washing the plates four times with PBS, 100 µl of a staining solution [containing 7.3 g of citric acid.$H_2O$, 11.86 g of $Na_2HPO_4.2H_2O$ per 1000 ml of distilled water to which a substrate for peroxidase has been added (40 mg of ortho-phenylene diamine dissolved in 100 ml of staining buffer to which 40 µl of perhydrol had been added)]. After 30 minutes, the reaction was stopped with 1M $H_2SO_4$ and the absorbance was measured at 492 nm.

Figure 2:
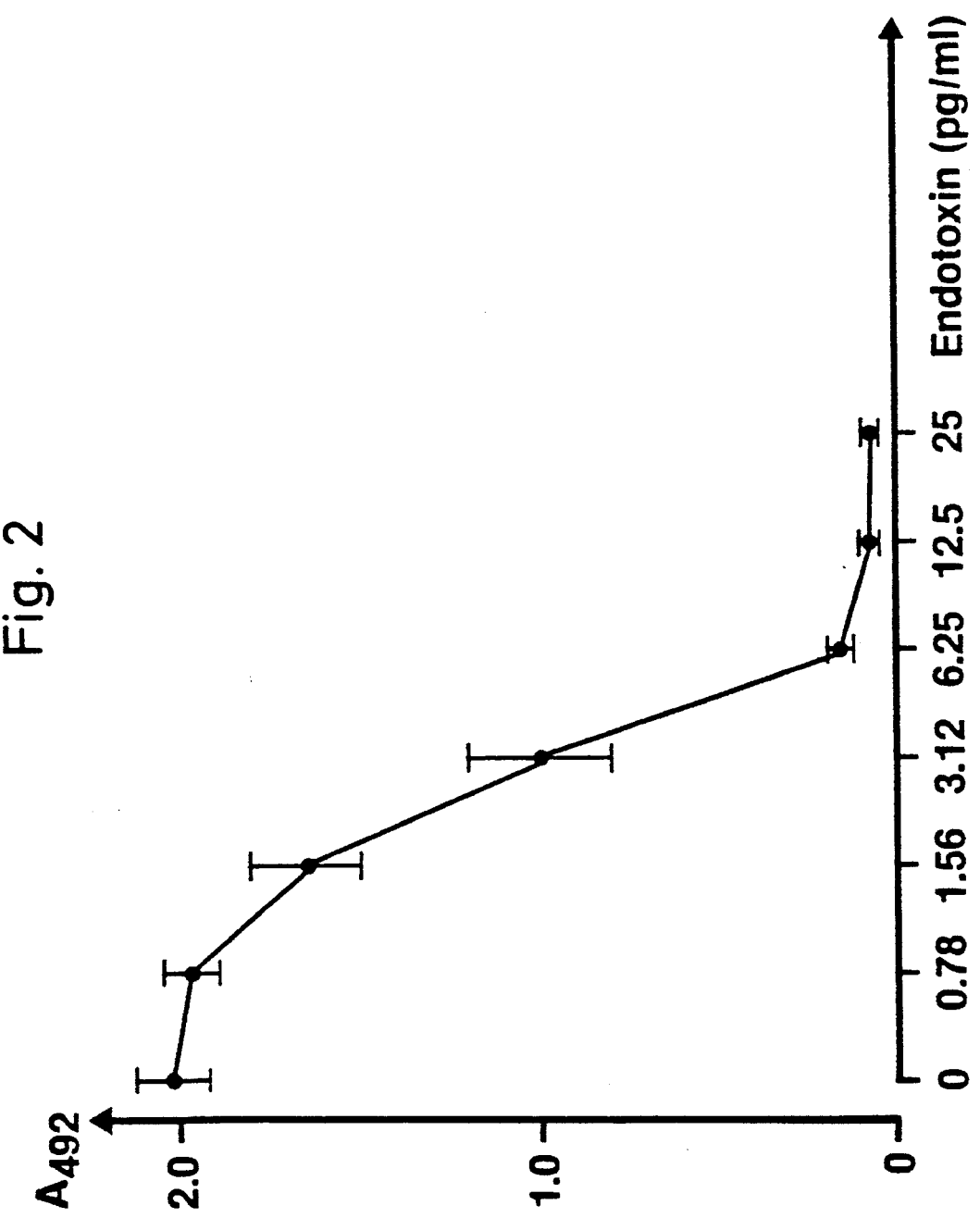
Figure 3:
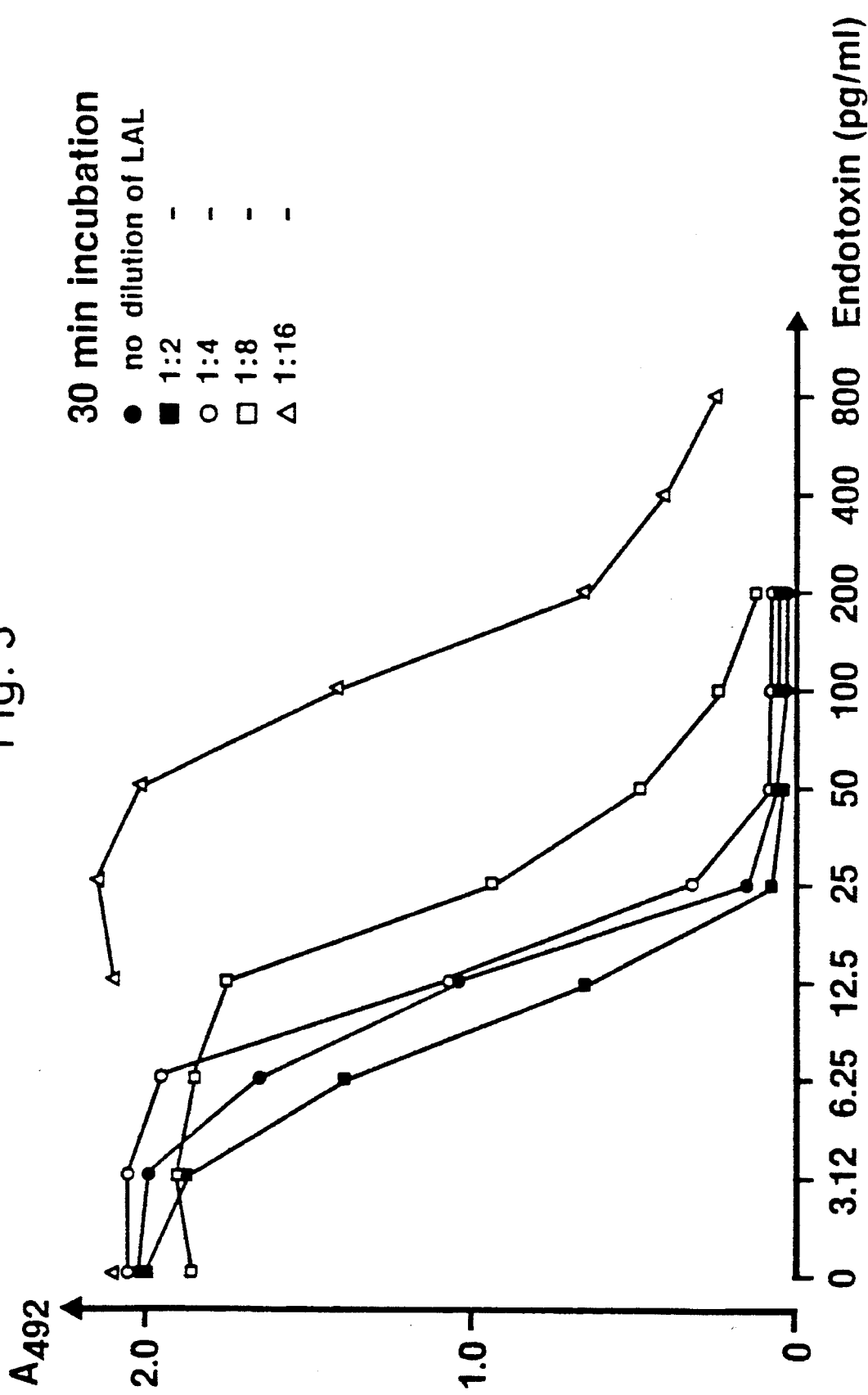
Figure 4:
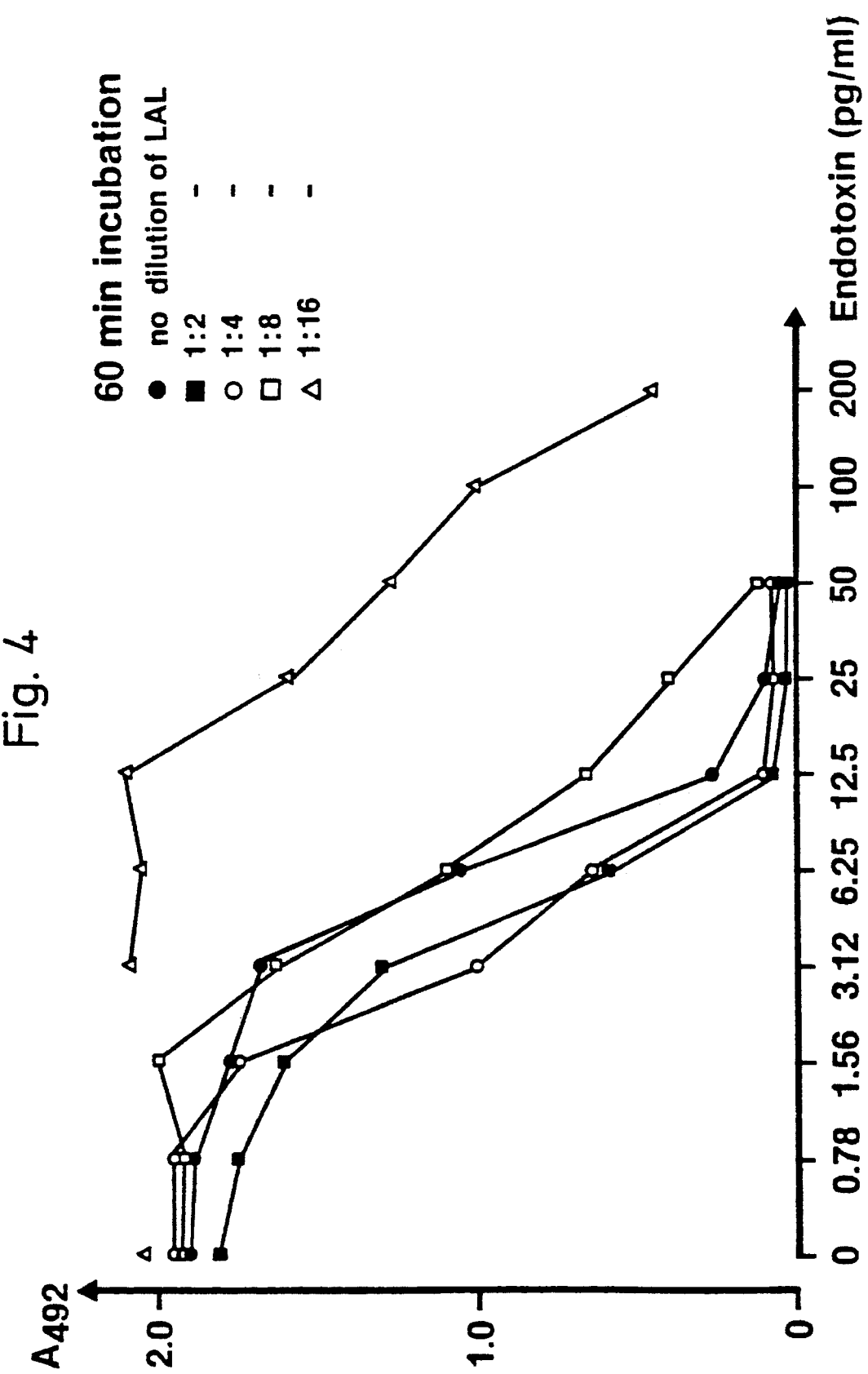
Figure 5:
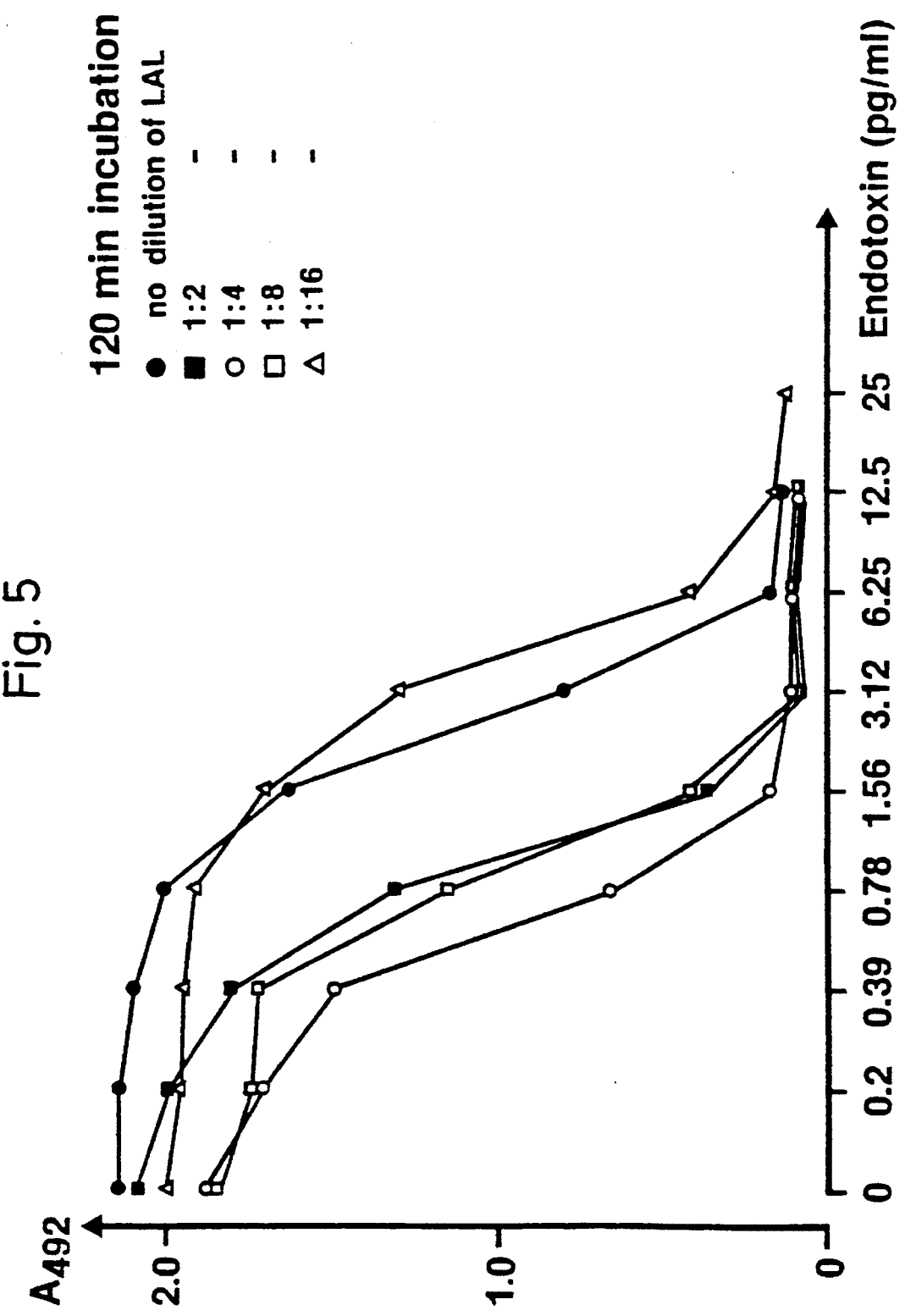

FIG. 2 is a standard curve showing the results of adding varying amounts of endotoxin to the sample. It appears from the curve that the sensitivity (detection range) of the method of the invention is in the range of 10–0.75 pg endotoxin/ml.

In the test described in this Example, coagulogen from the incubated mixture is coupled directly to the microtiter plate, and if any endotoxin is present, lower amounts of coagulogen will be present, resulting in a detectable decreases in the amount of bound antibody in the test, compared to an endotoxin-free control.

FIGS. 3–6 show reaction curves of reactions of LAL (coagulogen) with endotoxin under different conditions of incubation times and dilutions of LAL; it appears from the curves that (1) the detectability of endotoxin increased with increasing incubation times at all the dilutions of LAL, doing so more rapidly at the higher dilutions; (2) the same detectability at 1:4 dilution and below was observed after 30 minutes of incubation and the difference of the detectability between all the dilutions diminished with the increase of incubation time; (3) the wider span of the measurable concentration of endotoxin was seen in the curves where higher dilutions of LAL were used.

The ELISA test method of the invention was compared with a rocket-immunoelectrophoretic method (described in 43) and the conventional gel clot method (in which 0.1 ml of LAL reconstituted in pyrogen-free Tris-$Mg^{++}$ buffer was mixed in a glass test tube (10×75 mm) with 0.1 ml of endotoxin solution. The formation of a firm gel able to remain intact on inversion of the tube, was read as positive, all other results in negative). The results are shown in Table II.

TABLE II

Comparison of three endotoxin assay methods

| Endotoxin pg/ml | LAL-ELISA $A_{492}$ nm | LAL-RIE rocket (cm) | CLOT-GEL + or − |
|---|---|---|---|
| 0 | 2.02 | 4.7 | − |
| 0.78 | 1.96 | 4.2 | − |
| 1.56 | 1.64 | 3.0 | − |
| 3.12 | 1.00 | 1.5 | − |
| 6.25 | 0.15 | 0 | + |
| 12.5 | 0.07 | 0 | + |
| 25 | 0.07 | 0 | + |
| relative consumption of LAL | 1/40 | ½ | 1 |
| required time (hours) | 4 | 6 | 1 |
| quantitation | yes | yes | ? |
| applicability to plasma | yes | yes | ? |

It appears from Table II that the novel method compares favourably with the rocket-immunoelectrophoretic method, and is able to detect an 8 times lower concentration of endotoxin that the gel clot method.

Figure 6:
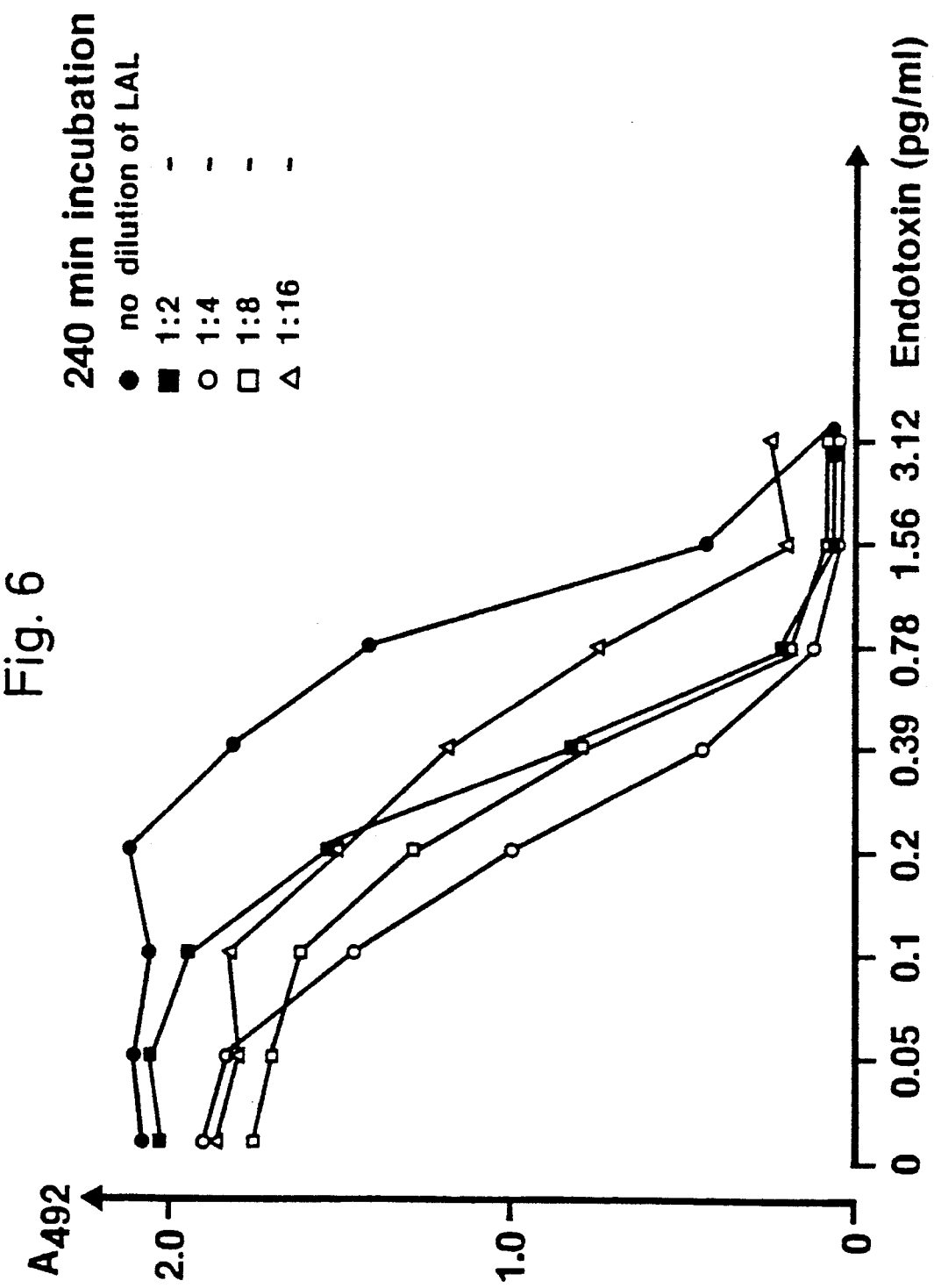

One of the advantages of the LAL-ELISA is that standard curves with desired sensitivity may be obtained from one batch of commercial LAL by adjusting dilution and incubation time of LAL. A sensitivity of 0.1 pg endotoxin has been achieved (FIG. 6).

With the official acceptance of the LAL test as a pyrogen test, a large demand for commercial LAL reagent has been witnessed. Since the only source of LAL is the horseshoe crab, an invertebrate which is gradually becoming extinct, the development of a sensitive LAL test which minimizes the consumption of LAL is of significant importance. The high sensitivity of the ELISA method to detect coagulogen (a value of $A_{492}$=2.0 was reached even when the original LAL was diluted ten thousand times) provides the possibility that very small amounts of LAL can be used in this method. It is calculated that, considering the volume and the dilution of LAL, only 1/160 of the amount of LAL used in the clot-gel method is needed in the LAL-ELISA when the same sensitivity is compared. Normally, the LAL-ELISA which has 10 times higher sensitivity than the clot-gel method requires about 1/40 of the amount of LAL used in the latter.

Besides the minimal consumption of LAL reagent, the LAL-ELISA requires very small amounts of samples. 10 µl of a sample is enough to perform a single test, in contrast to 100 µl of sample usually used in other LAL assays. This advantages may become significant in the cases where only a very small amount of sample is available.

EXAMPLE 4

Detection of endotoxin in a clinical sample

To demonstrate the ability of the method of the invention to detect the presence of endotoxin in a serum sample with the same high detection limit as in a buffer solution, USP reference standard endotoxin (cf. Example 3) was added to LPS-free human plasma diluted 10-fold in water to a final concentration of 200 pg/ml. The control was endotoxin in pyrogen-free water.

After the LPS had been added, the plasma was subjected to heat treatment for 15 minutes at 65° C., 10 minutes at 75° C and 5 minutes at 100° C., respectively, for three different samples.

The test was performed in duplicate in substantially the same way as described in Example 3 by preparing a series of dilutions of each of the plasma solutions obtained above using identically diluted and heated LPS-free plasma as the diluent. The results are shown in FIG. 7 from which it appears that treatment of plasma for 10 minutes at 75° C. was the optimum treatment for the quantitative determination of LPS. The $A_{492}$ values observed in the endotoxin-free water control were not significantly different from those observed in the plasma samples (within the limitation of the variation of the LAL-ELISA), indicating that the endotoxin levels in thee samples were below 4 pg endotoxin/ml (the detection limit) and that the LAL-ELISA was not interfered by the colour and turbidity of plasma. The results obtained demonstrate that the method of the invention is also useful as a sensitive method of assaying clinical samples for the presence of endotoxin.

EXAMPLE 5

Preparation of monoclonal antibody against coagulogen (TAL)

Using essentially the same procedure as described in Example 1, but replacing LAL with Tachypleus amoebocyte lysate (TAL) (*Tachypleus tridentatus*) as the starting material, monoclonal antibody against coagulogen from TAL was prepared. The antibody was reactive in the ELISA test described in Example 3.

EXAMPLE 6

Preparation of a biotin-monoclonal anti-coagulogen antibody conjugate

Biotin was conjugated with a monoclonal anti-coagulogen antibody prepared as described in Example 1 as follows:

1 ml of purified monoclonal antibody solution (1 mg IgG/ml) was dialyzed against 100 mM $NaHCO_3$ (pH 8.0) buffer at 4° C. overnight and then mixed with 5 µl of N-hydroxy-succinimidobiotin (40 mg/ml); Sigma Chemical Co.). After stirring at room temperature for 2 hours, the mixture was dialyzed against PBS (pH 7.3) at 4° C. overnight. The conjugate was added to an equal volume of glycerol (87%) and stored at −20° C.

This conjugate was employed in an ELISA procedure by adding 100 µl of a diluted incubated mixture of LAL and standard endotoxin (prepared as described in Example 3) to each well of a 96-well microtiter plate (NUNC, Denmark) and incubating for one hour at room temperature. After fur washes with washing buffer as described in Example 3, 100 µl of the monoclonal antibody-biotin conjugate diluted 1:2000 in dilution buffer was added. After incubation for 1 hour, the plate was washed 4 times. Then 100 µl of avidin-HRP conjugate (Sigma Chemical Co.) diluted 1:4000 in dilution buffer was added, and the plate was incubated for 1 hour. The plate was washed 4 times and 100 µl substrate solution was added (as described in Example 3). After 10 minutes of incubation, the reaction was stopped by the addition of 150 µl of 1M $H_2SO_4$. The absorbance was measured at $A_{492}$.

The ELISA using a HRP-monoclonal antibody conjugate involves one step less than that using the monoclonal antibody-biotin conjugate (the employment of HRP-avidin), but it was much easier to produce the biotin-monoclonal antibody conjugate than the HRP-monoclonal antibody conjugate. The conjugates were stable when kept below 0° C. Since 1 mg of the monoclonal antibody is enough for 20,000 single tests, the use of the monoclonal antibody will not make the LAL-ELISA expensive.

EXAMPLE 7

Testing of various different endotoxins and (1-3)-β-D-glucan by LAL-ELISA

The reference standard endotoxin was purchased from Whittaker M. A. Bioproducts, Inc. (10 ng/vial). Purified LPS (W) from *Salmonella minnesota*, *Escherichia coli* 0111:B4, *Escherichia coli* 055:B5, *Salmonella abortus* equi, *Salmonella typhimurium* and *Salmonella enteritidis* were purchased from Difco Laboratories (Detroit, Mich.). Highly purified LPS from *Escherichia coli* J5 and *Pseudomonas aeruginosa* were kindly provided by Dr. Anders Fomsgaard (Dept. Infectious Diseases, Rigshospitalet, Copenhagen).

All these LPS were reconstituted and diluted to the concentration of 1 mg/ml and frozen at −20° C. until use. Immediately prior to assay, various dilutions of LPS were prepared in endotoxin-free water. All the LPS assays were performed in duplicate and the values were averaged unless otherwise indicated.

(1-3)-β-D-glucan from *Alcaligenes faecalis* var. *myxogenes* IFO 13140 (Curdlan, Wako Pure Chemical Industries, Ltd., Osaka, Japan) was made endotoxin-free as described by Obayashi et al. (63). The concentrated solution (1 mg/ml) was stored at 4° C. until use.

A LAL-ELISA was carried out as described in Example 3, using a HRP-monoclonal antibody conjugate.

FIGS. 8 and 9 show the curves of the LAL-ELISA of 8 purified LPS and the curve of (1-3)-β-D-glucan. The LPS curves appear to have a sharp slope and to be parallel to one another, implying the intrinsic similarity of their reaction with LAL though a large difference of potency exists. The potency of (1-3)-β-D-glucan was at least 1000 times lower and the slope of its reaction curve was much flatter than that of LPS, indicating its much slower rate of reaction with LAL.

Several substances other than endotoxin have been reported to cause positive reactions at high concentrations (60,47). The (1-3)-β-D-glucan was shown to be able to react with LAL at the concentration of 1 ng/ml, being the most potent substance next to endotoxin (23). However, the conclusions of thee studies have frequently been questioned because of the possible contamination of endotoxin in the materials tested. In the present study, (1-3)-β-D-glucan was selectively examined using the LAL-ELISA and its reactivity was at least 1000 times lower than endotoxin. Furthermore, (1-3)-β-D-glucan seemed at behave in a manner intrinsically different from that of endotoxin, evidenced by its much slower rate of reaction with LAL. This may be explained by the finding of Morita et al. (23) that activation of LAL by (1-3)-β-D-glucan is through a pathway different from that of endotoxin. The two pathways are believed to have one step in common, namely the activation of proclotting enzyme. Thus, the activation of either of the two pathways will result in splitting of coagulogen and the loss of its antigenicity. The LAL-ELISA may be a useful tool to further study the substances able to react with LAL, since the reactions of endotoxin and (1-3)-β-D-glucan with LAL can be kinetically distinguished.

EXAMPLE 8

Detection of endotoxin in plasma

Venous blood from patients suspected of sepsis on admission were drawn into endotoxin-free glass tubes containing heparin (10 IU/ml of blood). Plasma prepared by centrifugation at 2000 rpm for 15 minutes was diluted 10-fold in endotoxin-free water and then subjected to heating at 75° C. for 10 minutes. The subsequent LAL-ELISA was performed as described in Example 3 except that the LAL was reconstituted as required by the manufacturer. The detection limit of the LAL-ELISA for endotoxins in plasma was 4 pg endotoxin/ml. The endotoxin concentrations in specimens were calculated from the standard curve with allowance being made for the dilution factor.

Table III shows the results of the determination of endotoxin in the plasma samples of 10 patients. The endotoxin levels in these septic patients were generally low and did not always correlate with the results of bacterial culture of blood or cerebrospinal fluid (CSF).

Patient No. 1 had a history of gonorrhoeal infection and was suspected of sepsis on admission. No bacteria were cultured but a significant increase of specific gonorrhoeal antibody was found in the blood. Patient No. 4 had gram-positive bacteria in the blood and CSF and died from septic shock 4 days after admission. Patient No. 8 was suspected of urosepsis and has significant bacteriuria. Patient No. 9 was suspected of meningococcal sepsis, but no bacteria were cultured because of treatment with penicillin before admission.

The presence of the very low concentrations of endotoxin in the blood of septic patients (Table III) shows the need for a sensitive LAL test. Interestingly, no normal plasma samples have been found which contained endotoxin higher than the detection limit of the LAL-ELISA (4 pg endotoxin/ml).

To conclude, the LAL-ELISA is a promising LAL test for the clinical detection of endotoxin because of its high sensitivity, less interference from plasma, minimized consumption of LAL reagent and test sample, good reproducibility and easy performance.

TABLE III

Detection of andotoxin in plasma samples from septic patients

| Pt. No. | Clinical diagnosis | Blood culture | CSF culture | LAL-ELISA pg CSE/ml | Other diag criteria |
|---|---|---|---|---|---|
| 1. | Gonorrhoea | neg | neg | 200 | Fever, Arthritis, Vasculitis, elevated GAT+ |
| 2. | Myelomatosis | P. aeruginosa | neg | 24 | |
| 3. | Meningitis purulenta | neg | N. meningitidis | 28 | Petecchia in the skin, Septic |
| 4. | Meningitis purulenta | S. pneumoniae | S. pneu- | 20 | K. pneumoniae in the lung |
| 5. | Meningitis purulenta | neg | M. men- | 8 | Petecchia in the skin, Septic |
| 6. | Febris typhoidea | S. typhosa | neg | 9 | |
| 7. | Meningitis purulenta | N. meningiti- | neg | 8 | Petecchia in the skin, septicemia |
| 8. | Meningitis | neg | neg | 8 | Petecchia in the skin, septic |
| 9. | Septicemia | neg | neg | 11 | >$10^5$ E. coli in the urine |
| 10. | Meningitis | neg | N. meningitidis | 9 | Petecchia in skin, septic |

+Gonorrhoea Antibody Titer

EXAMPLE 9

An assay for the endotoxin-inactivating activity of human plasma

The dose-dependent inactivation of LPS by human serum and plasma, Limulus plasma, LAL and polymyxin B was demonstrated by the LAL-ELISA described in Example 3.

To each endotoxin-free glass tube were successively added 50 μl each of the test samples (human serum and plasma, Limulus plasma, LAL and polymyxin B) and 50 μl of LPS (E. coli 0111:B4) variously diluted in sterile saline. The contents of each tube was mixed well and incubated at 37° C. for 1 hour. The above solutions were diluted at least 1000 times in endotoxin-free water to reach the LPS assay range (1 to 100 pg/ml) as well as to eliminate the possible interference of test samples with the subsequent LAL test. The quantitation of the residual LPS was made using LAL combined with an ELISA determination of coagulogen as described in Example 3.

All assays were performed independently at least twice and the values were averaged.

The reaction of LAL and LPS generated a linear curve between the absorbance and the LPS concentrations, determined by the LAL-ELISA using a monoclonal antibody against coagulogen as described in Example 3. The serum inhibition of the reaction was significant even when the serum sample was diluted 100 times. However, the inhibition disappeared totally when the serum was diluted more than 250 times.

FIG. 10 shows the dose-dependent inactivation of LPS by human serum, plasma, polymyxin B and Limulus plasma. No difference between EIA50 of human serum and plasma was observed. Limulus plasma appeared to have a significantly higher capacity of the inactivation of LPS than human plasma.

These results indicate that the LAL-ELISA described in Example 3 may be used to test plasma for its endotoxin-inactivating effect. Plasma found in this assay to possess a high endotoxin neutralizing effect may be administered to septic patients to promote recovery.

INSTRUCTIONS

It may be possible to detect the activation of Factory C by endotoxin by preparing purified Factor C according to the method disclosed by Nahamura et al. (64). A monoclonal antibody against the purified Factor C may then be prepared according to the procedure described in Example 1. This monoclonal antibody may then be conjugated as described in Examples 1 or 6 and used in a LAL-ELISA method as described in Example 3.

This procedure essentially corresponds to that described in Example 3 with the exception that the loss of antigenicity of Factor C rather than of coagulogen is determined as Factor C is converted to active Factor C on reacting with endotoxin.

It may also be possible to detect the activation of Factor G by (1-3)-β-D-glucan by preparing purified Factor G according to the method disclosed by Morita et al. (23), and preparing and conjugating a monoclonal antibody against Factor G by the procedure described in Examples 1 or 6. The conjugated monoclonal antibody may then be used in a LAL-ELISA method as described in Example 3.

It is contemplated that, once monoclonal antibodies against Factors C and G have been prepared, the same lysate may be employed for three different tests using Factor G, Factor C and coagulogen as the lysate components the presence or absence of which is detected. It is further contemplate that these tests may be carried out on the same microtiter plate thereby speeding up the procedure of, for instance, determining the cause of sepsis in septic patients.

REFERENCES

1. Levin J, Bang FB (1968). Clottable Protein in Limulus: its localization and kinetics of its coagulation by endotoxin.

*Thromb. Diath. Haemorrh.* 19, 186–197.

2. Levin J, Bang FB (1964). A description of cellular coagulogen in Limulus. *Bull. Johns. Hopkins Hosp.* 115, 337–345.

3. Bang FB (1958). A bacterial disease of *Limulus polyphemus. Bull. Johns. Hopkins Hosp.* 98, 325–351.

4. Jorgensen JH, Smith RF (1974). Measurement of bound and free endotoxin by the Limulus assay. *Proc. Soc. Exp. Biol. Med.* 146, 1024–1031.

5. Fleishman J. Fowlkes F (1982). A comparison of pyrogenicity of bacterial endotoxins from a variety of Gram-negative bacteria as determined by the LAL test. *Prog. Clin. Biol. Res.* 93, 131–140.

6. Weary ME, Donohue G, Pearson FC, Stony K (1980). Relative potencies of four reference endotoxin standards as measured by the Limulus amoebocyte lysate and USP rabbit pyrogen tests. *Appl. Environ. Microbiol.* 40, 1148–1151.

7. Food and Drug Administration 1983. Draft guideline for validation of the Limulus amoebocyte lysate test as an end-product endotoxin test for human and animal parenteral drugs, biological products, and medical devices. *Pharmacopeial Forum.* 9, 3012–3021.

8. Solum NO (1973). The coagulation of *Limulus polyphemus* hemocyates. A comparison of the clotted and no clotted forms of the molecule. *Throm. Res.* 2, 55–70.

9. Liu TY, Seid RC Jr. Tai JY, Liang S-M, Sakmar TP, Robbins JB (1979). Studies of Limulus lysate coagulation system. In *Biomedical Applications of the Horseshoe Crab (Limulidae)* (ed. E. Cohen), pp. 147–158. Alan R. Liss, New York.

10. Holme R, Solum NO (1973). Electron microscopy of the gel protein formed by clotting of *Limulus polyphemus* hemocyte extracts. *J. Ultrastructure Res.* 44, 329–338.

11. Tai JY, Seid RC, Huhn RD, Lui TY (1977). Studies on Limulus amoebocyte lysate. II. Purification of the coagulogen and the mechanism of clotting. *J. Biol. Chem.* 252, 4773–4776.

12. Nakamura S, Takagi T, Iwanaga S, Niwa M, Takahashi K (1976a). Amino acid sequence studies on the fragments produced from horseshoe crab coagulogen during gel formation: homologies with primate fibrinopeptide. *B. Biochem.* and *Biophys. Res. Commun.* 72, 902–908.

13. Nakamura S, Takagi T, Iwanaga S, Niwa M, Takahashi K (1976b). A clottable protein (coagulogen) from horseshoe crab hemocytes. Structural change of its polypeptide chain during gel formation. *J. Biochem.* 80, 649–652.

14. Gaffin SL (1976). The clotting of the lysed white cells of Limulus induced by endotoxin. I. Preparation and characterization of clot forming proteins. *Biorheologi.* 13, 273–280.

15. Shishikura F, Nakamura S, Takahashi K, Segiguchi K (1982). Horseshoe crab phylogeny based on amino acid sequence of the fibrinopeptide like peptide C. *J. Exp. Zool.* 223, 89–91.

16. Tai JY, Liu TY (1977). Studies on Limulus amoebocyte lysate. I. Isolation of proclotting enzyme. *J. Biol. Chem.* 252, 2178–2181.

17. Ohki M, Nakamura T, Morita T, Iwanaga S (1980). A new endotoxin-sensitive factor associated with hemolymph coagulation system of horseshoe crab (Limulidae). *FEBS Letters* 120, 217–220.

18. Nakamura S, Levin J (1982a). Fractionation of Limulus amoebocyte lysate. Characterization of activation of the proclotting enzyme by an endotoxin-mediated activator. *Biochim. Biophys. Acta.* 707, 217–225.

19. Nakamura S, Levin J (1982b). Endotoxin-mediated Limulus proclotting enzyme activator and detection of previously undescribed protease (protease N). *Biochem. Biophys. Res. Commun.* 108, 1619–1623.

20. Liang SM, Sakmar TP, Liu TY (1980). Studies of Limulus amoebocyte lysate. III. Purification of an endotoxin-binding protein from Limulus amoebocyte membranes. *J. Biol. Chem.* 255, 5586–5590.

21. Tanaka S, Nakamura T, Morita T, Iwanaga S (1982). Limulus anti-LPS factor: an anticoagulant which inhibits the endotoxin-mediated activation of the Limulus coagulation system. *Biochem. Biophys. Res. Commun.* 105, 717–723.

22. Kakinuma A, Asano T, Torh H, Sugino Y (1981). Gelation of Limulus amoebocyte lysate by an antitumor (1-3)-β-D-glucan. *Biochem. Biophys. Res. Commun.* 101, 434–439.

23. Morita T, Tanaka S, Nakamura T, Iwanaga S (1981). A new (1-3)-β-D-glucan mediated coagulation pathway found in Limulus amoebocytes. *FEBS Letters* 129, 318–321.

24. Albaugh BR, Chander CB (1982). Automated methodology for the Limulus amoebocyte lysate (LAL) assay using the multiskan microplate reader, pp. 183–194. In Watson S, Levin J, Novitsky TJ (eds), Endotoxins and their detection with the Limulus lysate test. Alan R. Liss, Inc., New York.

25. Fujita Y, Nakahara C (1982). Preparation and application of a new endotoxin determination kit, Pyrodick, using a chromogenic substrate, pp. 173–182. In Watson S, Levin J, Novitsky TJ (eds), Endotoxins and their detection with the Limulus lysate test. Alan R. Liss, Inc., New York.

26. Nandan R, Brown DR (1977). An improved in vitro pyrogen test: to detect picograms of endotoxin contamination in intravenous fluids using Limulus amoebocyte lysate. *J. Lab. Clin. Med.* 89, 910–918.

27. Dunczak JA, Cotter R, Dastoli FR (1979). Quantiative detection of endotoxin by nephelometry, pp. 403–414. In E. Cohen (ed.), Biomedical Applications of the Horseshoe Crab (Limulidae). Alan R. Liss, Inc., New York.

28. Jorgensen JH, Reichler AS (1982). Automation of the Limulus amoebocyte lysate pyrogen testing. *J. Parenter. Sci. Technol.* 36, 11–16.

29. Nowitsky TJ, Ryther SS, Case MJ, Watson (1982). Automated LAL testing of parentral drugs in Abbot MS-2. *J. Parenter. Sci. Technol.* 36, 11–16.

30. Ditter VB, Becker KP, Urbascheck R, Urbascheck B (1982). Detection of endotoxin in blood and other specimens of evaluation of photometrically registered LAL reaction kinetics in microtiter plates. *Prog. Clin. Biol. Res,* 93, 385–392.

31. Frauch P (1974). Slide test as a micro-method of a modified Limulus endotoxin test. *J. Pharm. Sci.* 63, 808–809.

32. Goto H, Watanabe M, Nakamura S (1977). Studies on a simple Limulus test, a slide method. *Jpn. J. Exp. Med.* 47, 523–524.

33. Goto H, Nakamura S (1979). Dry up method as a revised Limulus test with a new technique for gelation inhibitor removing. *Jpn. J. Exp. Med.* 49, 19–25.

34. Melvaer KL, Fystro D (1982). Modified micromethod of the Limulus amoebocyte lysat assay for endotoxin. *Appl. Environ. Microbiol.* 43, 493–494.

35. Flowers DJ (1979). A microtechnique for endotoxin assay by using Limulus lysate. *Med. Lab. Sci.* 36, 171–176.

36. Okuguchi S (1978). Improvement of the micromethod for the Limulus lysate test. *Microbiol. Immunol.* 22, 113–121.

38. Kreeftenberg JG, Loggen HG, Van Ramshorst JD, Beuvery EC (1977). The Limulus amoebocyte lysate test micromethod and application in the control of sera and vaccines. *Dev. Biol. Standard.* 34, 15–20.

39. Gardi A, Arpagaus GR (1980). Improved microtechnique for endotoxin assay for the Limulus amoebocyte lysate test. *Anal. Biochem.* 109, 382–385.

40. Prior RB, Spagna VA (1979). Adaptation of a microdilution procedure to the Limulus lysate assay for endotoxin. *J. Clin. Microbiol.*, 10, 394–395.

41. Harris NS, Feinstein R (1979). The LAL-bead assay for endotoxin, pp. 264–274. In E. Cohen (ed.), Biomedical Applications of the Horseshoe crab (Limulidae), Alan R. Liss, Inc., New York.

42. Munford RS (1978). Quantitative Limulus lysate assay for endotoxin activity: aggregation of radioiodinated coagulogen monomoners. *Anal. Biochem.* 91, 509–515.

43. Baek L (1983). New, sensitive rocket immunoelectrophoretic assay for measurement of the reaction between endotoxin and Limulus amoebocyte lysate. *J. Clin. Microbiol.* 17, 1013–1020.

44. Elin RJ, Wolff SM (1973). Nonspecificity of the Limulus amoebocyte lysate test: positive reactions with polynucleotides and proteins. *J. Infect. Dis.* 128, 349–352.

45. Wildfeuer A, Heymer B, Schleifer KH, Haferkamp O (1974). Investigations on the specificity of the Limulus test for the detection of endotoxin. *Appl. Microbiol.* 28, 867–871.

46. Brunson KW, Watson DW (1976). Limulus amoebocyte lysate reaction with streptococcal pyrogenic exotoxin. *Infect. Immun.* 14, 1256–1258.

47. Mikami T, Nagase T, Matsumoto T, Suzuki S, Suzuki M (1982). Gelation of Limulus amoebocyte lysate by simple polysaccharides. *Microbiol. Immunol.* 26, 403–409.

48. Suzuki M, Mikami T, Matsumoto T, Suzuki S (1977) Gelation of Limulus lysate by synthetic dextran derivatives. *Microbiol. Immunol.* 21, 419–425.

49. Platica M, Harding W, Hollander VP (1978). Dithiols simulate endotoxin in the Limulus reaction. *Experientia* 34, 1154–1155.

50. Fine DH, Kessler RE, Tabak LA, Shockman GD (1977). Limulus lysate activity of lipoteichoic acid. *J. Dent. Res.* 56, 1500.

51. Seid RC Jr., Smith PF, Guevarra G, Hochstein HD, Barile MF (1980). Endotoxin-like activities of mycoplasmal lipopolysaccharides (lipoglycans) *Infect. Immun.* 29, 990–994.

52. Weinberg JB, Smith PF, Kahane I (1980). Bacterial lipopolysaccharides and mycoplasmal lipoglycans: a comparison between their abilities to induce macrophage-mediate tumor cell killing and Limulus amoebocyte lysate clotting. *Biochem. Biophys. Res. Commun.* 97, 493–499.

53. Smith SM, Hill JO, Snyder IS, Burrel R (1978). Mitogenicity of cell wall fractions of *Micropolyspora faeni*. *Ann. Allergy* 40, 12–14.

54. Lewis VJ, Thacher L, Mitchell SH (1979). Demonstration of Chlamydia endotoxin-like activity. *J. Gen. Microbiol.* 144, 215–216.

55. Felton SC, Prior RB, Spagna VA, Kreier JP (1980). Evaluation of *Plasmodium berghei* for endotoxin by the Limulus lysate assay. *J. Parasitol.* 66, 846–847.

56. Wexler H, Oppenheim JD (1979). Isolation, characterization, and biological properties of an endotoxin-like material from the gram-positive organism *Listeria monocytogenes*. *Infect. Immun.* 23, 845–857.

57. Elin RJ (1979). Clinical utility of the Limulus test with blood, CSF and synovial fluid, pp. 279–292. In E. Cohen (ed.), *Biomedical Applications of the Horseshoe Crab* (Limulidae). Alan R. Liss, Inc., New York.

58. Tubbs H (1980). Endotoxin in human and murine malaria. *Trans. R. Soc. Trop. Med. Hyg.* 74, 121–123.

59. Galloway RE, Levin J, Butler T, Naff GB, Goldsmith GH, Saito H, Awoke S, Wallace CK (1977). Activation of protein mediators of inflammation and evidence for endotoxemia in *Borrelia recurrentis* infection. *Am. J. Med.* 63, 933–938.

60. Bæk L, Høiby N, Hertz JB, Espersen F (1985). Interaction between Limulus amoebocyte lysate and soluble antigens from *Pseudomonas aeruginosa* and *Staphylococcus aureus* studied by quantitative immunoelectrophoresis. *J. Clin. Microbiol.* 22, 229–237.

61. Jorgensen JH (1986). Clinical applications of the Limulus amoebocyte lysate test. In Proctor RA (ed.), *Handbook of Endotoxin* 4: *Clinical aspects of endotoxin shock.* Elsevier Science Publisher B.V., Amsterdam.

62. Wilson MB and PK Nakane, in *Immunofluorescence and Related Techniques* (W. Knapp, H. Holubar and G. Wick, eds.), Elsevier/North-Holland, Amsterdam, 1978, pp. 215–221.

63. Obayashi T, et al., *Clinica Chimica Acta* 149, 1985, pp. 55–65.

64. Nakamura T, Morita T and Iwanaga S. Lipopolysaccharide-sensitive serine protease zymogen (Factor C) found in Limulus hemocytes. Isolation and characterization. *Eur. J. Biochem.* 154, 1986 pp. 511–521.

We claim:

1. A monoclonal antibody which specifically binds to coagulogen of a limulus amoebocyte lysate, but does not bind to coagulogen of said limulus amoebocyte lysate which has been contacted with activated clotting enzyme of said limulus amoebocyte lysate.

2. A monoclonal antibody which specifically binds to a product of a coagulogen of a limulus amoebocyte lysate wherein said product is formed upon contact of aid coagulogen with activated clotting enzyme of said limulus amoebocyte lysate, but which does not bind to said coagulogen that has not been contacted with activated clotting enzyme of said limulus amoebocyte lysate.

3. A monoclonal antibody produced by a hybridoma isolated by a method comprising:

i) producing a pool of hybridomas secreting monoclonal antibodies by immunizing an animal with coagulogen of a limulus amoebocyte lysate or with an antigen comprising an immunologic determinant of aid coagulogen;

ii) testing said pool of hybridomas for secretion of a monoclonal antibody that specifically binds to said coagulogen of a limulus amoebocyte lysate or with an antigen comprising an immunologic determinant of said coagulogen;

iii) testing said pool of hybridomas for secretion of a monoclonal antibody that does not bind to said coagulogen of a limulus amoebocyte lysate wherein said limulus amoebocyte lysate has been contacted with a lipopolysaccharide of a gram-negative bacterium; and iv) isolating those hybridomas which secrete a monoclonal antibody that specifically binds to said coagulogen of a limulus amoebocyte lysate or with an antigen comprising an immunologic determinant of said coagulogen and that does not bind to said coagulogen of a limulus amoebocyte lysate wherein said limulus amoebocyte lysate has been contacted with a lipopolysaccharide of a gram-negative bacterium.

4. A monoclonal antibody produced by a hybridoma isolated by a method comprising:
  i) producing a pool of hybridomas secreting monoclonal antibodies by immunizing an animal with coagulogen of a limulus amoebocyte lysate or with an antigen comprising an immunologic determinant of aid coagulogen;
  ii) testing said pool of hybridomas for secretion of a monoclonal antibody that specifically binds to said coagulogen of a limulus amoebocyte lysate or with an antigen comprising an immunologic determinant of said coagulogen;
  iii) testing said pool of hybridomas for secretion of a monoclonal antibody that does not bind to said coagulogen of a limulus amoebocyte lysate wherein said limulus amoebocyte lysate has been contacted with a lipopolysaccharide of a gram-negative bacterium; and
  iv) isolating those hybridomas which secrete a monoclonal antibody that specifically binds to said coagulogen of a limulus amoebocyte lysate wherein said limulus amoebocyte lysate has been contacted with a lipopolysaccharide of a gram-negative bacterium and that does not bind to said coagulogen of a limulus amoebocyte lysate or with an antigen comprising an immunologic determinant of said coagulogen.

5. A monoclonal antibody according to claim 2, which specifically binds to C-peptide.

6. A monoclonal antibody according to claim 2, which specifically binds to non-covalently cross-linked coagulin.

7. A monoclonal antibody according to claim 2, which specifically binds to covalently cross-linked coagulin.

8. A test kit for determining the presence of a compound that initiates a limulus amoebocyte lysate clotting cascade, in a sample, comprising at least one monoclonal antibody according to claim 1 or 2 and a container.

9. A test kit according to claim 8, wherein said at least one monoclonal antibody includes a monoclonal antibody that specifically binds to C-peptide.

10. A test kit according to claim 8, which comprises two or more monoclonal antibodies.

11. A test kit according to claim 8, wherein said at least one monoclonal antibody is covalently labeled.

12. A test kit according to claim 11, wherein said label is selected from the group consisting of an enzyme, a fluorescent substance, a chemiluminescent substance, a chromophore, a radioactive isotope and a complexing agent.

13. A test kit according to claim 12, wherein said label is an enzyme selected from the group consisting of a peroxidase, a phosphatase, β-galactosidase, urease, glucose oxidase, carbonic anhydrase, acetylcholinesterase, glucoamylasae, lysozyme, malate dehydrogenase, glucose-6-phosphate dehydrogenase and ribonuclease.

14. A test kit according to claim 13, which further comprises a substrate for said enzyme, wherein said substrate is selected from the group consisting of a chromogenic substrate, a substrate forming a fluorescent product and a substrate forming a chemiluminescent product.

15. A test kit according to claim 12, wherein said fluorescent substance is selected from the group consisting of 4-methylumbelliferyl phosphate, 4-methylumbelliferyl-D-galactopyranoside and 3-(p-hydroxphenyl)-propionic acid.

16. A test kit according to claim 14, wherein said enzyme and substrate are together peroxidase and eosin or luciferase and a substrate for luciferase.

17. A test kit according to claim 12, wherein said label is isoluminol.

18. A test kit according to claim 12, wherein said label is a radioactive substance selected from the group consisting of $^{125}I$, $^{3}H$, $^{35}P$, $^{131}I$ and $^{14}C$.

19. A test kit according to claim 12, wherein said label is a complexing agent selected from the group consisting of biotin, Protein A and a lectin.

20. A test kit according to claim 8, which further comprises a solid support.

21. A test kit according to claim 20, wherein said solid support is selected from the group consisting of a plastic, nitrocellulose, cyanogen-bromide activated paper, 1-3(nitrobenzyloxymethyl)pyridium chloride activated paper, diazobenzyloxymethyl paper, nitrobenzylmethyl paper, aminobenzyloxymethyl paper, a silicone polymer and a silicate.

22. A test kit according to claim 8, which comprises both a labeled antibody and an unlabeled antibody.

23. A test kit according to claim 8, which further comprises an endotoxin standard.

24. A test kit according to claim 8, which further comprises pyrogen-free water.

25. A test kit according to claim 8, which further comprises a limulus amoebocyte lysate or hemolymph.

26. A method for producing a monoclonal antibody which specifically binds to coagulogen of a limulus amoebocyte lysate, but does not bind to coagulogen of said limulus amoebocyte lysate which has been contacted with activated clotting enzyme of said limulus amoebocyte lysate, comprising:
  i) producing a pool of hybridomas secreting monoclonal antibodies by immunizing an animal with coagulogen of a limulus amoebocyte lysate or with an antigen comprising an immunologic determinant of said coagulogen;
  ii) testing said pool of hybridomas for secretion of a monoclonal antibody that specifically binds to said coagulogen of a limulus amoebocyte lysate or with an antigen comprising an immunologic determinant of said coagulogen;
  iii) testing said pool of hybridomas for secretion of a monoclonal antibody that does not bind to said coagulogen of a limulus amoebocyte lysate wherein said limulus amoebocyte lysate has been contacted with a lipopolysaccharide of a gram-negative bacterium; and
  iv) isolating those hybridomas which secrete a monoclonal antibody that specifically binds to said coagulogen of a limulus amoebocyte lysate or with an antigen comprising an immunologic determinant of said coagulogen and that does not bind to said coagulogen of a limulus amoebocyte lysate wherein said limulus amoebocyte lysate has been contacted with a lipopolysaccharide of a gram-negative bacterium;
  v) culturing a hybridoma obtained from step (iv); and
  vi) isolating a monoclonal antibody from the hybridoma culture.

27. A method for isolating a monoclonal antibody which specifically binds to a product of a coagulogen of a limulus amoebocyte lysate wherein said product is formed upon contact of said coagulogen with activated clotting enzyme of said limulus amoebocyte lysate, but which does not bind to said coagulogen that has not ben contacted with activated clotting enzyme of said limulus amoebocyte lysate, comprising:

i) producing a pool of hybridomas secreting monoclonal antibodies by immunizing an animal with said product of a coagulogen of a limulus amoebocyte lysate or with an antigen comprising an immunologic determinant of said coagulogen product;

ii) testing said pool of hybridomas for secretion of a monoclonal antibody that specifically binds to said product of a coagulogen of a limulus amoebocyte lysate or with an antigen comprising an immunologic determinant of said coagulogen product;

iii) testing said pool of hybridomas for secretion of a monoclonal antibody that does not bind to said coagulogen of a limulus amoebocyte lysate wherein said limulus amoebocyte lysate has been contacted with a lipopolysaccharide of a gram-negative bacterium; and iv) isolating those hybridomas which secrete a monoclonal antibody that specifically binds to said product of a coagulogen of a limulus amoebocyte lysate wherein said limulus amoebocyte lysate has been contacted with a lipopolysaccharide of a gram-negative bacterium and that does not bind to said coagulogen of a limulus amoebocyte lysate or with an antigen comprising an immunologic determinant of said coagulogen;

v) culturing a hybridoma obtained from step (iv); and vi) isolating a monoclonal antibody from the hybridoma culture.

* * * * *

UNITED STATES PATENT AND TRADEMARK OFFICE
CERTIFICATE OF CORRECTION

PATENT NO. : 5,591,628
DATED : Jan. 7, 1997
INVENTOR(S) : Baek et al.

It is certified that error appears in the above-indentified patent and that said Letters Patent is hereby corrected as shown below:

Title page, item "[22] Filed:", please change the filing date from "May 28, 1990" to --May 28, 1993--.

Signed and Sealed this

Seventeenth Day of June, 1997

Attest:

*Attesting Officer*

BRUCE LEHMAN

*Commissioner of Patents and Trademarks*